(12) United States Patent
Yamanaka et al.

(10) Patent No.: US 11,313,836 B2
(45) Date of Patent: Apr. 26, 2022

(54) SYSTEM, METHOD AND COMPUTER PROGRAM PRODUCT FOR GAS ANALYSIS

(71) Applicant: Ball Wave Inc., Sendai (JP)

(72) Inventors: Kazushi Yamanaka, Sendai (JP); Nobuo Takeda, Sendai (JP); Shingo Akao, Sendai (JP); Toshihiro Tsuji, Sendai (JP); Toru Oizumi, Sendai (JP); Hideyuki Fukushi, Sendai (JP); Tatsuhiro Okano, Sendai (JP); Nagisa Sato, Sendai (JP); Yusuke Tsukahara, Sendai (JP)

(73) Assignee: BALL WAVE INC, Sendai (JP)

( * ) Notice: Subject to any disclaimer, the term of this patent is extended or adjusted under 35 U.S.C. 154(b) by 161 days.

(21) Appl. No.: 16/650,404

(22) PCT Filed: Jan. 30, 2019

(86) PCT No.: PCT/JP2019/003269
§ 371 (c)(1),
(2) Date: Mar. 25, 2020

(87) PCT Pub. No.: WO2019/151362
PCT Pub. Date: Aug. 8, 2019

(65) Prior Publication Data
US 2020/0225190 A1    Jul. 16, 2020

Related U.S. Application Data

(60) Provisional application No. 62/624,139, filed on Jan. 31, 2018.

(51) Int. Cl.
*G01N 29/02*    (2006.01)
*G01N 29/032*    (2006.01)
(Continued)

(52) U.S. Cl.
CPC ......... *G01N 29/022* (2013.01); *G01N 29/032* (2013.01); *G01N 29/221* (2013.01);
(Continued)

(58) Field of Classification Search
CPC .. G01N 29/022; G01N 29/032; G01N 29/221; G01N 29/222; G01N 29/348;
(Continued)

(56) References Cited

U.S. PATENT DOCUMENTS

| 2002/0177232 A1 | 11/2002 | Melker et al. |
| 2010/0018288 A1 | 1/2010 | Yamanaka et al. |
| 2017/0307567 A1 | 10/2017 | Yamanaka et al. |

FOREIGN PATENT DOCUMENTS

| JP | H09-210975 A | 8/1997 |
| JP | 2007-309752 A | 11/2007 |
| JP | 2008-245003 A | 10/2008 |

OTHER PUBLICATIONS

N. Takeda et al., "Deep Sub-micro mol mol Water-Vapor Measurement by Dual-Ball SAW Sensors for Temperature Compensation", International Journal of Thermophysics, Aug. 23, 2015, pp. 3440-3452, vol. 36, No. 12, Springer, New York, USA; Cited in the EESR issued on Mar. 3, 2021.

(Continued)

*Primary Examiner* — Tarun Sinha
(74) *Attorney, Agent, or Firm* — METROLEX IP LAW GROUP, PLLC

(57) ABSTRACT

A collimated beam (23) of a surface acoustic wave propagates on a piezoelectric substrate (22) while passing through sensitive film (25) to adsorb a sensing gas. Signal processing unit (40) transmits an exciting burst signal to sensor electrode (24) to excite the collimated beam (23), receives first and second returned burst signals after the collimated beam (23) has propagated, and calculates a target gas parameter by a target leakage factor of the background gas and a relation (Continued)

between reference gas parameters and reference leakage factors of reference gases, the leakage factor is provided by first and second attenuations of the first and second returned burst signals, respectively, using waveform data of the first and second returned burst signals.

19 Claims, 15 Drawing Sheets

(51) Int. Cl.
    *G01N 29/22*     (2006.01)
    *G01N 29/34*     (2006.01)
    *G01N 33/00*     (2006.01)

(52) U.S. Cl.
    CPC ......... *G01N 29/222* (2013.01); *G01N 29/348* (2013.01); *G01N 33/005* (2013.01); *G01N 2291/0215* (2013.01); *G01N 2291/101* (2013.01)

(58) Field of Classification Search
    CPC .......... G01N 29/4436; G01N 29/4472; G01N 2291/0215; G01N 2291/101; G01N 2291/0212; G01N 2291/0423; G01N 2291/0255; G01N 2291/0256
    See application file for complete search history.

(56) References Cited

OTHER PUBLICATIONS

Kazushi Yamanaka et al., "Multiple Organic Gas Detection by the Ball Surface Acoustic Wave Sensor", 2010 First International Conference on Sensor Device Technologies and Applications, SENSORDEVICES, Jul. 18, 2010, pp. 120-123, IEEE, Piscataway, NJ, USA; Cited in the EESR issued on Mar. 3, 2021.
Extended European search report (EESR) dated Mar. 3, 2021 in a counterpart European patent application.
Kazushi Yamanaka et al., "Ultramultiple Roundtrips of Surface Acoustic Wave on Sphere Realizing Innovation of Gas Sensors", Institute of Electrical and Electronics Engineers (IEEE) Transactions on Ultrasonics, Ferroelectrics, and Frequency Control, Apr. 2006, pp. 793-801, vol. 53 No. 4, Cited in the Specification.
A.J. Slobodnik, Jr., "Attenuation of Microwave Acoustic Surface Waves Due to Gas Loading", J. Appl. Phys., Jun. 1972, pp. 2565-2568, vol. 43, No. 6, Cited in the Specification, Cited in the ISR and Written Opinion of the ISA.
S. J. Martin et al., "Dynamics and Response of Polymer-Coated Surface Acoustic Wave Devices: Effect of Viscoelastic Properties and Film Resonance", Jul. 15, 1994, Analytical Chemistry, pp. 2201-2219, vol. 66, No. 14, Cited in the Specification.
A. Witkowski et al., "Analysis of compression and transport of the methane/hydrogen mixture in existing natural gas pipelines", International Journal of Pressure Vessels and Piping, 2018, pp. 24-34, vol. 166, Cited in the Specification.
Yamanaka, Kazushi et al., "Simultaneous measurement of gas concentration and temperature by the ball surface acoustic wave sensor", Japanese Journal of Applied Physics, 2017, pp. 07JC04-1-6, vol. 56, Cited in the ISR and Written Opinion of the ISA.

- Flowing target gas — S100
- Transmitting burst signal — S101
- Receiving burst signals — S102
- Measuring attenuations — S103
- Calculating gas parameter — S104
- Estimating gas species or gas concentration — S105

| Gas | Molecular weight $M$ | Heat capacity ratio $\gamma$ | Gas parameter $\sqrt{\gamma M}$ |
|---|---|---|---|
| $H_2$ | 2 | 1.40 | 1.67 |
| He | 4 | 1.66 | 2.58 |
| $CH_4$ | 16 | 1.30 | 4.56 |
| $NH_3$ | 17 | 1.33 | 4.75 |
| $N_2$ | 28 | 1.40 | 6.26 |
| $C_2H_6$ | 30 | 1.33 | 6.32 |
| Air | 28.8 | 1.40 | 6.35 |
| $C_3H_8$ | 44 | 1.33 | 7.65 |
| Ar | 40 | 1.67 | 8.17 |
| $C_4H_{10}$ | 58 | 1.33 | 8.78 |

| Gas | Molecular weight $M$ | Heat capacity ratio $\gamma$ | Gas parameter $G=\sqrt{\gamma M}$ | Leakage factor $\Delta\alpha_L$ (dB/m) | Measured gas parameter $G^*=\sqrt{\gamma M}^*$ | Relative error (%) |
|---|---|---|---|---|---|---|
| $N_2$ | 28 | 1.40 | 6.26 | 116.23 | Calibration | ---- |
| Ar | 40 | 1.67 | 8.17 | 133.83 | Calibration | ---- |
| X1 ($CH_4$) | 16 | 1.30 | 4.56 | 99.35 | 4.43 | -2.89 |
| X2 (Air) | 28.8 | 1.40 | 6.35 | 117.19 | 6.36 | 0.228 |

| Gas | Molecular weight $M$ | Heat capacity ratio $\gamma$ | Gas parameter $G=\sqrt{\gamma M}$ | Leakage factor $\Delta\alpha_L$ (dB/m) | Measured gas parameter $G^*=\sqrt{\gamma M}^*$ | Relative error (%) |
|---|---|---|---|---|---|---|
| X3($N_2$) | 28 | 1.40 | 6.26 | 115.99 | 6.23 | −0.421 |
| X4(Ar) | 40 | 1.67 | 8.17 | 133.66 | 8.15 | −0.227 |
| X5 ($CH_4$) | 16 | 1.30 | 4.56 | 99.45 | 4.44 | −2.66 |
| X6 (Air) | 28.8 | 1.40 | 6.35 | 117.31 | 6.38 | 0.434 |

| Gas | Molecular weight $M$ | Molar specific heat $C_V$ (J/mol K) | Molar specific heat $C_P$ (J/mol K) | Ratio of specific heat $\gamma = C_P/C_V$ | Gas parameter $G \equiv \sqrt{\gamma M}$ |
|---|---|---|---|---|---|
| He | 4.0 | 12.47 | 20.78 | 1.67 | 2.58 |
| $N_2$ | 28.0 | 20.76 | 29.10 | 1.40 | 6.26 |

SYSTEM, METHOD AND COMPUTER PROGRAM PRODUCT FOR GAS ANALYSIS

TECHNICAL FIELD

The present invention relates to a system, a method and a computer program product for gas analysis using a surface acoustic wave (SAW) sensor, and especially, using a ball SAW sensor.

BACKGROUND ART

In oil and gas industry, trace moisture sensors in natural gas are used, but variation of composition in background gases degrades the precision of the sensors. The composition variation takes place when the gas production condition is changed. Also, the composition of background gases is an important parameter for evaluating the heat value. Thus, the composition of background gases is usually measured by gas chromatography (GC), but GC is large and expensive apparatus.

As recited in non patent literature (NPL) 1, a ball SAW sensor has been developed and applied to a trace moisture sensor. In the ball SAW sensor, the SAW excited on a spherical surface with a specific condition may be naturally collimated, and multiple roundtrips along the equator of the ball can be realized. Thus, the ball sensor based on the multiple-roundtrips effect of the SAW may provide high performance, such as high sensitivity and wide sensing range. Further, in NPL 2, SAW attenuation due to propagation at the boundary between a solid and a monatomic gas is described. Further, in NPL 3, frequency dependence of SAW attenuation by a gas is described.

In a new technology for hydrogen transport, hydrogen is injected into natural gas and carried in natural gas pipeline system, as reported in NPL 4. In the technology, rapid hydrogen concentration measurement is needed in a concentration range up to 10%. Though sound velocity measurement, thermal conductivity measurement, and infra-red spectroscopy are used for analysis of natural gases, fast and precise hydrogen gas sensor is not available.

CITATION LIST

Non Patent Literature

[NPL 1]: K. Yamanaka, et al.: Institute of Electrical and Electronics Engineers (IEEE) Transactions on Ultrasonics, Ferroelectrics, and Frequency Control, vol. 53 (2006) pp. 793
[NPL 2]: A. J. Slobodnik, Jr.: J. Appl. Phys., 43, 2565 (1972)
[NPL 3]: S. J. Martin, et al.: Anal. Chem. 66, 2201 (1994).
[NPL 4]: A. Witkowski, et al.: J. Press. Vessels Pip. 166, 24 (2018).

SUMMARY OF INVENTION

Technical Problem

In view of the above problems, an object of the present invention is to provide a system, a method and a computer program product for gas analysis, which facilitate a high precision measurement of gas species and concentration in a short time.

Solution to Problem

A first aspect of the present invention inheres in a system for gas analysis, includes (a) a sensor having: a piezoelectric substrate, a sensor electrode configured to generate a collimated beam of a surface acoustic wave of first and second frequencies, which propagates on the piezoelectric substrate, and a sensitive film configured to adsorb a sensing gas contained in a background gas, the sensitive film is deposited in a position where the collimated beam passes through; and (b) a signal processing unit having: a signal generator configured to transmit an exciting burst signal to the sensor electrode so as to excite the collimated beam, a signal receiver configured to receive first and second returned burst signals of the collimated beam through the sensor electrode after the collimated beam has propagated on the piezoelectric substrate, the first returned burst signal having the first frequency and the second returned burst signal having the second frequency, and a data processor configured to calculate a target gas parameter by a target leakage factor of the background gas and a relation between reference gas parameters and reference leakage factors of reference gases, the leakage factor is provided by a first attenuation of the first returned burst signal and a second attenuation of the second returned burst signal using waveform data of the first and second returned burst signals.

A second aspect of the present invention inheres in a method for gas analysis using a surface acoustic wave sensor having a sensor electrode generating a surface acoustic wave and a sensitive film adsorbing a sensing gas, on a piezoelectric substrate, includes (a) flowing a background gas containing the sensing gas into a sensor cell having the surface acoustic wave sensor in place; (b) transmitting an exciting burst signal to the sensor electrode so as to excite a collimated beam of the surface acoustic wave of first and second frequencies, which propagates on the piezoelectric substrate while passing through the sensitive film deposited in a position where the collimated beam passes through; (c) receiving first and second returned burst signals of the collimated beam through the sensor electrode after the collimated beam has propagated on the piezoelectric substrate, the first returned burst signal having the first frequency and the second returned burst signal having the second frequency; and (d) calculating a target gas parameter by a target leakage factor of the background gas and a relation between reference gas parameters and reference leakage factors of reference gases, the leakage factor is provided by a first attenuation of the first returned burst signal and a second attenuation of the second returned burst signal using waveform data of the first and second returned burst signals.

A third aspect of the present invention inheres in a computer program product embodied on a computer-readable medium for gas analysis using a surface-acoustic-wave sensor having a sensor electrode generating a surface-acoustic-wave and a sensitive film adsorbing a sensing gas, on a piezoelectric substrate, includes (a) instructions to flow a background gas containing the sensing gas into a sensor cell having the surface-acoustic-wave sensor in place; (b) instructions to transmit an exciting burst signal to the sensor electrode so as to excite a collimated beam of the surface-acoustic-wave of first and second frequencies, which propagates on the piezoelectric substrate while passing through the sensitive film deposited in a position where the collimated beam passes through; (c) instructions to receive first and second returned burst signals of the collimated beam through the sensor electrode after the collimated beam has propagated on the piezoelectric substrate, the first returned burst signal having the first frequency and the second returned burst signal having the second frequency; and (d) instructions to calculate a target gas parameter by a target leakage factor of the background gas and a relation between reference gas parameters and reference leakage factors of reference gases, the leakage factor is provided by a first attenuation of the first returned burst signal and a second attenuation of the second returned burst signal using waveform data of the first and second returned burst signals.

Advantageous Effects of Invention

According to the present invention, it is possible to provide the system, the method and the computer program product for gas analysis, which facilitate a high precision measurement of gas species and concentration in a short time.

DESCRIPTION OF EMBODIMENTS

Figure 1:
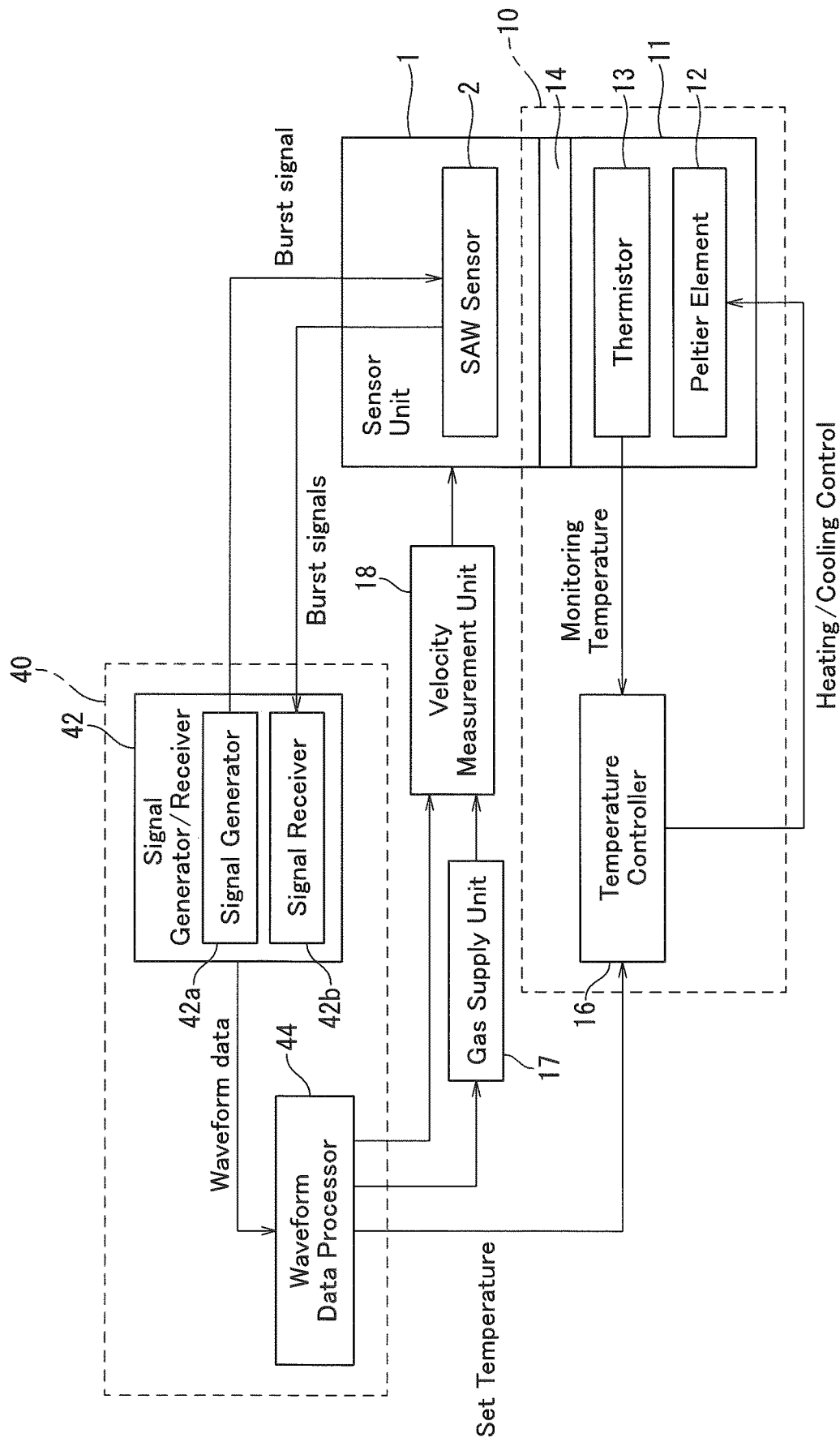
FIG. 1 is a block diagram illustrating an example of a gas analyzer using a SAW sensor according to an embodiment of the present invention.

Embodiments of the present invention will be described below with reference to the drawings. In the descriptions of the following drawings, the same or similar reference numerals are assigned to the same or similar portions. However, the drawings are diagrammatic, and attention should be paid to a fact that the relations between thicknesses and plan view dimensions, the configuration of the apparatus and the like differ from the actual data. Thus, the specific thicknesses and dimensions should be judged by considering the following descriptions. Also, even between the mutual drawings, the portions in which the relations and rates between the mutual dimensions are different are naturally included. Also, the first and second embodiments as described below exemplify the apparatuses and methods for embodying the technical ideas of the present invention, and in the technical ideas of the present invention, the materials, shapes, structures, arrangements and the like of configuration parts are not limited to the followings.

In the following description, α, β, γ, Δ and ρ represent Greek alphabet characters, respectively. And, the "horizontal" direction or the "vertical" direction is simply assigned for convenience of explanation and does not limit the technical spirit of the present invention. Therefore, for example, when the plane of paper is rotated 90 degrees, the "horizontal" direction is changed to the "vertical" direction and the "vertical" direction is changed to the "horizontal" direction. When the plane of paper is rotated 180 degrees, the "left" side is changed to the "right" side and the "right"

side is changed to the "left" side. Therefore, various changes can be added to the technical ideas of the present invention, within the technical scope prescribed by claims.

(Construction of Gas Analyzer)

Figure 2:
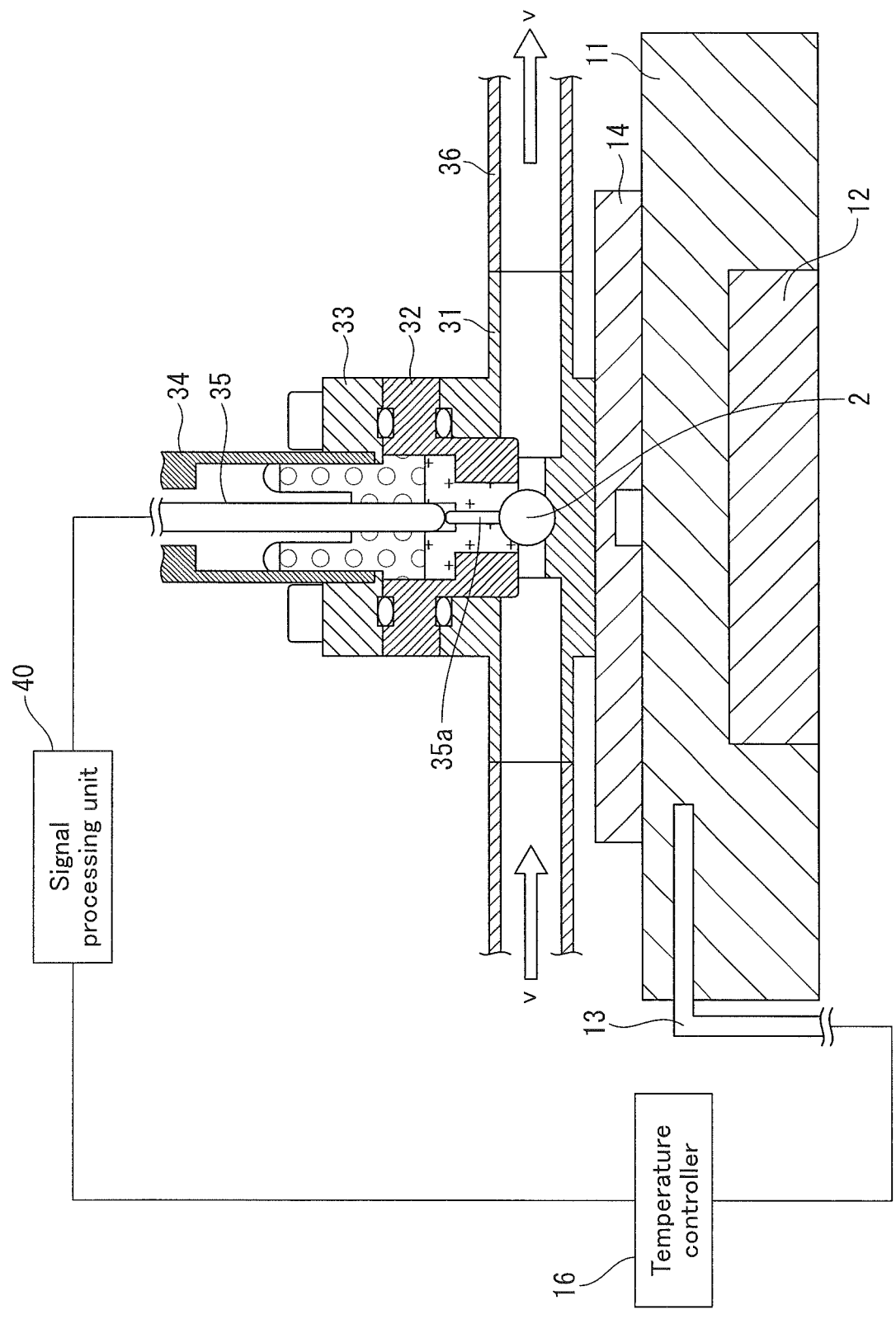
FIG. 2 is a schematic cross sectional view illustrating an example of a system for the gas analysis using the SAW sensor according to the embodiment of the present invention.

As illustrated in FIG. 1, a system for gas analysis, or a gas analyzer, pertaining to an embodiment of the present invention includes a sensor unit 1, a temperature controller 16, a gas supply unit 17, a velocity measurement unit 18 and a signal processing unit 40. The sensor unit 1, as illustrated in FIG. 2, has a SAW sensor 2, which is a ball SAW sensor, embedded in a tubular sensor cell 31, wherein the tubular sensor cell 31 is fixed on a plate-shaped adapter 14 disposed on a block-shaped holder 11. As the SAW sensor 2 has spherical shape, the inner structure of the sensor cell 31 has a concave configuration for mounting a lower portion of the SAW sensor 2 in a tubular topology of the sensor cell 31. An electrode-holder base 32 is fixed on the sensor cell 31, such that the bottom of the electrode-holder base 32 is inserted in an inner wall of a window, which is vertically cut at the top wall of the sensor cell 31. An opening of a canal, which penetrates vertically through the bottom of the electrode-holder base 32, partially covers an upper portion of the SAW sensor 2. Furthermore, a top of the electrode-holder base 32 is capped by a sensor-cell cap 33.

The SAW sensor 2 is connected to a rod-shaped external electrode 35 through a contact pin 35a along a vertical direction via the canal at the bottom of the electrode-holder base 32. The external electrode 35 is held in a hollow space of a vertically aligned cylindrical electrode holder 34, the bottom of which is inserted in an inner portion of the sensor-cell cap 33. A sensing gas containing in a background gas, for example, a humid gas, is introduced into the sensor cell 31 through a horizontally aligned tubing 36 with a gas flow rate v, so that the humid gas can touch the surface of the SAW sensor 2. The gas flow rate v is typically 0.1 L/min to 1 L/min.

Figure 3:
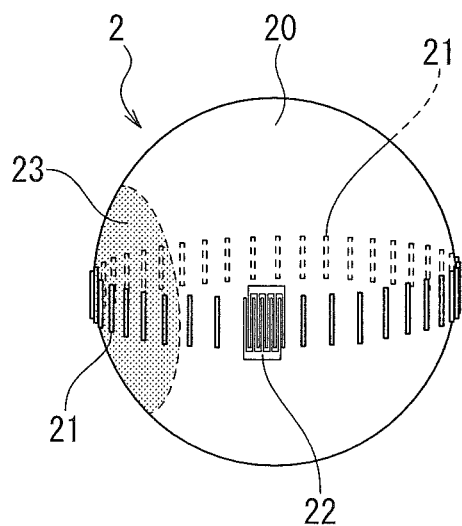
FIG. 3 is a schematic view illustrating an example of the SAW sensor used in the gas analyzer according to the embodiment of the present invention.

As illustrated in FIG. 3, the SAW sensor 2 may have a sensor electrode 22 and a sensitive film 23 arranged in predetermined areas on the surface of a homogeneous piezoelectric ball 20. As a three-dimensional base body, the piezoelectric ball 20 provides a homogeneous material sphere, on which a circular orbital band for propagating a SAW can be defined. The sensor electrode 22 generates a collimated beam 21 of the SAW, which includes a fundamental wave of a first frequency and a harmonic wave of a second frequency, propagates repeatedly through the circular orbital path defined on the piezoelectric ball 20 while passing through the sensitive film 23 deposited on the orbital path. The sensitive film 23 can be formed on almost the entire surface of the orbital band, which defines the orbital path on the three-dimensional base body. Because the sensitive film 21 is configured to react with specific gas molecules, the sensitive film 21 adsorbs water vapor in the sensing gas-to-be-measured.

For the piezoelectric ball 20, a crystal sphere, such as quartz, langasite ($La_3Ga_5SiO_{14}$), lithium niobate ($LiNbO_3$), lithium tantalate ($LiTaO_3$), piezoelectric ceramics (PZT), bismuth germanium oxide ($Bi_{12}GeO_{20}$) and the like, may be used. For the sensitive film 23, a silica ($SiO_x$) film and the like may be used. The sensor electrode 22 may be deposited in an opening of the sensitive film 23, the opening exposes a part of the surface of the piezoelectric ball 20, in a configuration such that the opening is formed on a part of the equator of the homogeneous piezoelectric ball 20. For the sensor electrode 22, an interdigital electrode (IDT) using a chromium (Cr) film and the like may be used as an electroacoustic transducer. In the case of a sphere of single crystal such as the homogeneous piezoelectric ball 20, a SAW orbiting route is limited to a specific orbital band having a constant width, depending on type of crystal material. The width of the orbital band may be increased or decreased depending on anisotropy of the crystal.

There are no diffraction losses during roundtrips around the piezoelectric ball 20, and only propagation loss due to material attenuation. The collimated beam 21 is scheduled to propagate many turns passing through the sensitive film 23, which is configured to adsorb water molecules. Because the adsorbed water molecules change the propagation characteristic of the SAW, the changes due to adsorbed water molecules in the humid gas on the sensitive film 23 can be integrated every turn through the multiple roundtrips. Thus, even though the sensitive film 23 may be so thin as to adsorb the small amount of the water vapor, measurement accuracy of gas analysis may be increased.

The suitable relationship between the first frequency $f_1$ of the fundamental wave and the second frequency $f_2$ of the harmonic wave shall be represented by $f_2=nf_1$, where n=3 or 5. That is, in the system for gas analysis pertaining to the embodiment of the present invention, the harmonic wave is the third-order harmonic wave or the fifth-order harmonic wave. Thus, when the first frequency $f_1$ is 80 MHz, the second frequency $f_2$ is 240 MHz for the third-order harmonic wave or 400 MHz for the fifth-order harmonic wave. Appropriate range of the first frequency $f_1$ for the piezoelectric ball 20 of 3.3 millimeters diameter may be from 60 MHz to 100 MHz, and the most suitable first frequency $f_1$ may be 80 MHz. The first frequency $f_1$ is inversely proportional to the diameter of the piezoelectric ball 20.

For example, the SAW sensor 2 may be fabricated as described below. A pattern of an IDT of about 150 nanometers thick Cr film is deposited on a surface of a quartz ball having a diameter of 3.3 millimeters. The IDT has a pair of bus bars, and a plurality of electrode fingers extending from the bus bars, respectively. The electrode fingers overlap each other with a cross width Wc, and each electrode finger has a width Wf and a periodicity P. The cross width Wc, the width Wf and the periodicity P are designed as 364 micrometers, 6.51 micrometers and 10.0 micrometers, respectively, for the natural collimation of 80 MHz SAW (refer to NPL 1).

The IDT on the quartz ball having 3.3 millimeters diameter can generate 80 MHz SAW as a fundamental wave and 240 MHz SAW as a third-order harmonic wave. Then a silica film is synthesized by using a sol-gel method and coated on the surface of the quartz ball as follows: 3.47 grams of tetraethoxysilane (TEOS), 0.75 grams of isopropanol (IPA), and 1.50 grams of 0.1N hydrochloric acid (HCl) are mixed and stirred by sonication (27, 45, 100 kHz, 60 minutes). TEOS is polymerized by hydrolysis and resulted in $SiO_x$. After sonication, the mixture is diluted with IPA and 0.5 mass % $SiO_x$ solution is obtained. The surface of propagation route of SAW is coated with the $SiO_x$ solution using a spin coating. Condition of the spin coating is 3000 rpm for 20 seconds. The thickness of $SiO_x$ film is confirmed as 1029 nanometers from measurement using interference microscope.

An RF voltage is applied to the sensor electrode 22 via an electrode pad (not illustrated) arranged around the north-pole, which is a top of the piezoelectric ball 20 in FIG. 3, using the contact pin 35a attached on the bottom of the external electrode 35. Another electrode pad (not illustrated) arranged around the south-pole, which is a bottom of the piezoelectric ball 20 in FIG. 3, is in contact with the grounded sensor cell 31.

Figure 4:
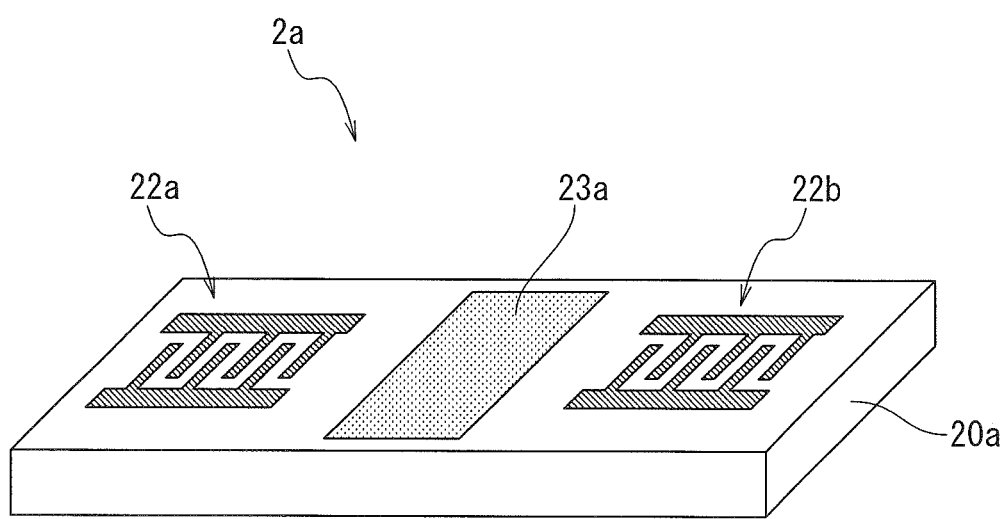
FIG. 4 is a schematic view illustrating another example of the SAW sensor used in the gas analyzer according to the embodiment of the present invention.

In the above description, a ball SAW sensor is used as the SAW sensor 2, but a planar SAW sensor 2a illustrated in FIG. 4 may be used. The planar SAW sensor 2a have an input electrode 22a, a sensitive film 23a and an output electrode 22b, which are arranged in predetermined areas on the surface of a homogeneous piezoelectric substrate 20a.

As illustrated in FIG. 2, the temperature controller 16 is connected to a Peltier element 12, which is held in a lower portion of the holder 11 at a position just below the SAW sensor 2, and a thermistor 13 is inserted in the holder 11 at a side position of the holder 11. Furthermore, the temperature controller 16 is connected to the thermistor 13. The Peltier element 12 is used for heating and cooling the SAW sensor 2 in the sensor cell 31 through the adapter 14. The thermistor 13 is used for detecting a monitoring temperature $T_{th}$ of the holder 11. The temperature controller 16 controls the Peltier element 12 by using the monitoring temperature $T_{th}$. As illustrated in FIG. 2, the thermistor 13 cannot be directly inserted into the sensor cell 31 to prevent leakage of gases through the sensor cell 31. Note that, although the thermistor 13 is used for detecting the monitoring temperature $T_{th}$ in the first embodiment, but other thermometers, such as a thermocouple and the like, may be used.

Figure 5:
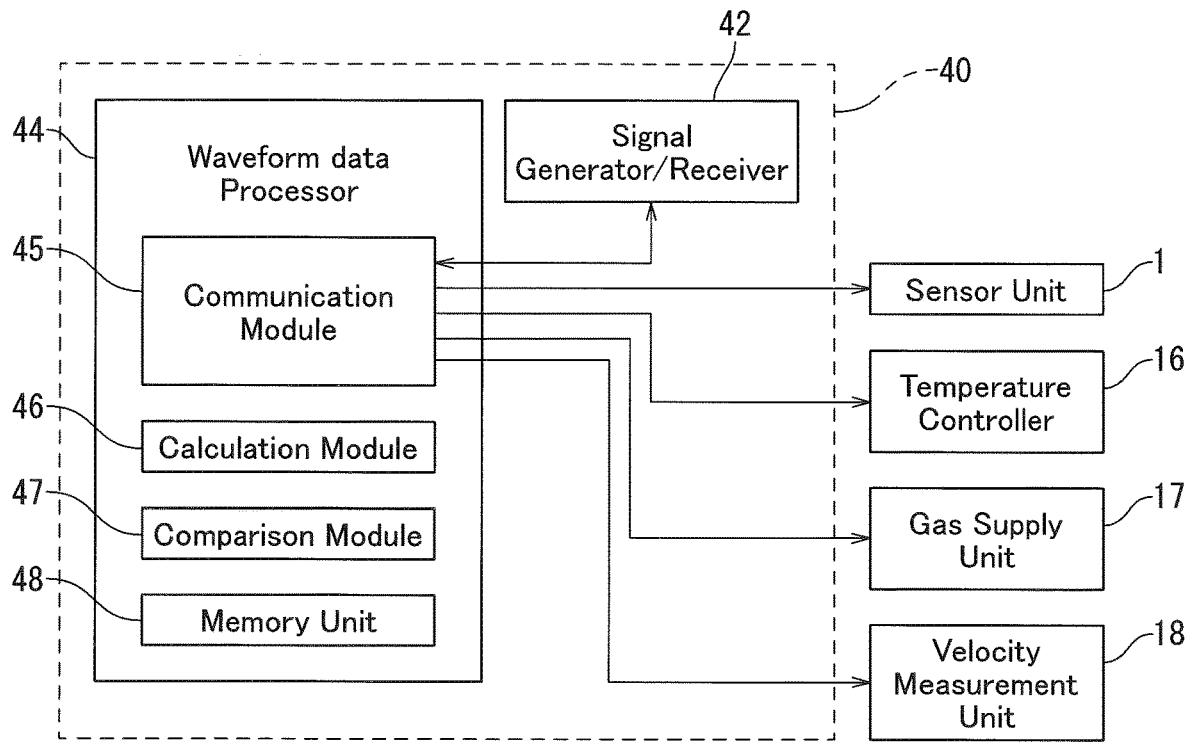
FIG. 5 is a block diagram illustrating an example of the signal processing unit in the system for the gas analysis according to the embodiment of the present invention.

The signal processing unit 40, as illustrated in FIG. 1, includes a signal generator and a signal receiver (hereinafter the set of the signal generator and the signal receiver is referred as the "signal generator/receiver") 42 and a waveform data processor 44. The signal generator/receiver 42 includes a signal generator 42a, and a signal receiver 42b. As illustrated in FIG. 5, the waveform data processor 44 includes a communication module (communication logical circuit) 45, a calculation module (calculation logical circuit) 46, a comparison module (comparison logical circuit) 47, and a memory unit 48 for logical hardware resources of a computer system. The communication module 45 of the waveform data processor 44 sends a predetermined "set temperature" or a control temperature for the Peltier element 12 to the temperature controller 16, which are illustrated in FIGS. 1 and 2. And, the communication module 45 sends instructions for flowing a gas into the sensor cell 31 to the sensor unit 1 and the gas supply unit 17 illustrated in FIGS. 5 and 6. Moreover, the communication module 45 sends instructions for measuring a sound velocity in the gas supplied from the gas supply unit 17 to the velocity measurement unit 18. In addition, when the velocity measurement of the gas is not necessary, the gas may be directly supplied to the sensor unit 1 from the gas supply unit 17.

Moreover, the communication module 45 sends instructions to the signal generator/receiver 42 so that the signal generator 42a illustrated in FIG. 1 transmits an exciting burst signal to the sensor electrode 22 of the SAW sensor 2 and the sensor electrode 22 can excite the collimated beam 21 of a SAW propagating around the piezoelectric ball 20 illustrated in FIG. 3. And furthermore, the communication module 45 sends instructions to the signal generator/receiver 42 so that the signal receiver 42b illustrated in FIG. 1 can receive returned burst signals of the collimated beam 21 through the sensor electrode 22 after the collimated beam 21 has propagated a predetermined number of turns around the piezoelectric ball 20 illustrated in FIG. 3. As illustrated in FIG. 5, the signal generator/receiver 42 transmits waveform data of the returned burst signals to the waveform data processor 44.

The calculation module 46 of the waveform data processor 44 calculates a gas parameter by using first and second attenuations in amplitudes of the SAWs of the first and second frequencies, respectively, using the waveform data of the returned burst signals. The comparison module 47 of the waveform data processor 44 compares the calculated gas parameter with data of gas parameters for various gases in order to determine gas species. The memory unit 48 of the waveform data processor 44 stores a program for driving the waveform data processor 44 to implement processing of the waveform data for calculating the gas parameter. Also, the memory unit 48 stores the data of gas parameters for various gases, and data obtained during the calculation and analysis of the gas during the operation of the waveform data processor 44.

The waveform data processor 44 may be a part of central processing unit (CPU) of a general purpose computer system, such as a personal computer (PC) and the like. The waveform data processor 44 may include an arithmetic logic unit (ALU) that performs arithmetic and logic operations, a plurality of registers that supply operands to the ALU and store the results of ALU operations, and a control unit that orchestrates the fetching (from memory) and execution of instructions by directing the coordinated operations of the ALU. The communication module 45, the calculation module 46, and the comparison module 47 implementing the ALU may be discrete hardware resources such as logical circuit blocks or the electronic circuitry contained on a single integrated circuit (IC) chip, or alternatively, may be provided by virtually equivalent logical functions achieved by software, using the CPU of the general purpose computer system.

In addition, the program for the waveform data processor 44 for the gas analysis is not limited to being stored in the memory unit 48 installed in the waveform data processor 44. For example, the program may be stored in an external memory. Moreover, the program may be stored in a computer readable medium. By reading the computer readable medium in the memory unit 48 of the computer system, which includes the waveform data processor 44, the waveform data processor 44 implements coordinated operations for the gas analysis, in accordance with a sequence of instructions recited in the program. Here, the "computer readable medium" refers to a recording medium or a storage medium, such as an external memory unit of a computer, a semiconductor memory, a magnetic disk, an optical disk, a magneto optical disk, and a magnetic tape, on which the program can be recorded.

(Basis of Analysis)

In NPL 2, leaky attenuation coefficient $\alpha_L$ of SAW is given by $$\alpha_L = \frac{f}{\rho_S V_S^2} \sqrt{\frac{\rho}{K_G}} \tag{1}$$

where f is a frequency, $\rho_s$ is a density of the piezoelectric ball 20, $V_s$ is a SAW velocity of the piezoelectric ball 20, $\rho$ is a density of the gas and $K_G$ is a compressibility of the gas. Substituting known relations $$\rho = MP/RT \text{ and } K_G = 1/(\gamma P) \tag{2}$$

into Eq. (1), it becomes $$\alpha_L = \frac{fP}{\rho_S V_S^2} \sqrt{\frac{\gamma M}{RT}}, \tag{3}$$

where M is a molecular weight of the gas, P is a pressure of the gas, R is a gas constant, T is a temperature and γ is the heat capacity ratio which is ratio of the specific heat at constant pressure to the specific heat at constant volume of the gas.

In a SAW sensor shown in FIG. 1, burst of two frequencies $f_1$ and $f_2$ is transmitted and attenuations $\alpha_1$ and $\alpha_2$ at each frequency is measured. Then a leakage factor $\Delta\alpha_L$ is defined as $$\Delta\alpha_L[(f_2/f_1)^u\alpha_1-\alpha_2]/l \tag{4}$$

where the superscript "u" is an index to describe the frequency dependence of the attenuation by the sensing gas, which is 1.8 or more and 2.3 or less, and l is the SAW propagation length.

A model is constructed for the calculation purpose with $$\alpha_1=a_0F_1^z+a_1(w)F_1^u+a_2F_1^y, \text{ and} \tag{5}$$

$$\alpha_2=a_0F_2^z+a_1(w)F_2^u+a_2F_2^y, \tag{6}$$

where $F_1=f_1/f_0$, $F_2=f_2/f_0$, $f_0$ is a reference frequency, and with the propagation length l of the SAW, $$a_0=\alpha_L'=[f_0Pl/(\text{Rho [Greek]}_s V_s^2)][\text{Gamma [Greek]}M/(RT)]^{1/2} \tag{7}$$

is an attenuation caused by a leakage to the background gas at frequency $f_0$, the superscript "z" is a frequency dependence index of leaky attenuation $\alpha_L'$, $a_1(w)$ is a loss by the sensing gas, w is a concentration of the sensing gas, $a_2$ is a device loss due to scattering at the sensor electrode 22, etc., the superscript "y" is a frequency dependence index of the device loss. The index z is normally equal to 1.0 according to NPL2, as in Eq. (1) and Eq. (3), and $\alpha_L'=\alpha_L$ is assumed as described later. However, the index z may be 0.8 or more and 1.3 or less. It is noted that the concept and process of modifications to Eq. (8) and following equations of Eq. (8) in the case of using z other than z=1 is obvious to a person having skills in the technical field.

Figures 7, 8:
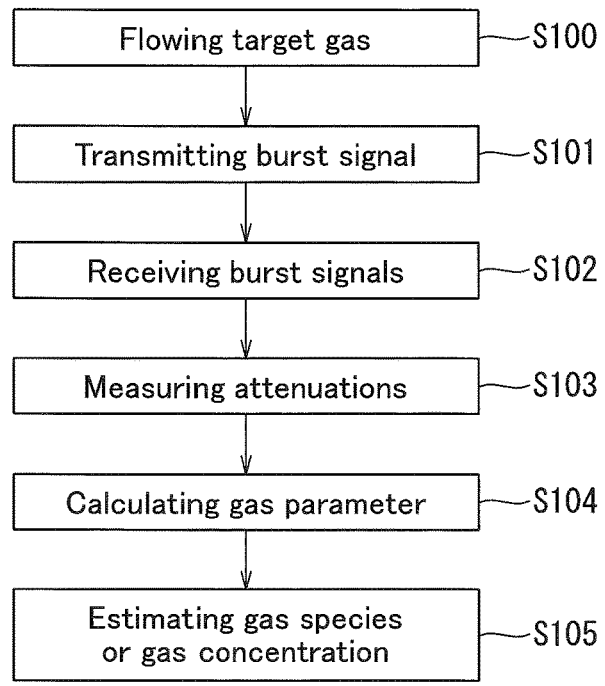
FIG. 7 is a flow chart illustrating an example of a method for the gas analysis according to the embodiment of the present invention.
FIG. 8 is a table illustrating examples of gas parameters for typical light gasses according to the embodiment of the present invention.

It is noted that $[\gamma M]^{1/2}$ in Eq. (7) is an important parameter describing property of the background gas, and thus it is defined as a gas parameter, here. Examples of gas parameters G, or "reference gas parameters", for typical light gasses, each of which is calculated by molecular weight M and heat capacity ratio γ of each gas, are listed in a table of FIG. 8. It is noted that the order of magnitude of the gas parameter is not identical to that of molecular weight, nor that of heat capacity ratio.

Subtracting Eq. (6) from Eq. (5) multiplied by $(F_2/F_1)^u$, the leakage factor $\Delta\alpha_L$ is related to the losses by $$\Delta\alpha_L=\alpha_L(F_1^{1-x}F_2^x-F_2)+(a_2/l)(F_1^{y-x}F_2^x-F_2^y) \tag{8}$$

As a special case, we define $F_2=3F_1$, $F_1=1$ and the loss to be a viscoelastic loss with u=2 (refer to NPL 3). Then, $$\Delta\alpha_L=\alpha_L(3^x-3)+(a_2/l)(3^x-3^y)=6\alpha_L+(a_2/l)(9-3^y). \tag{9}$$

From Eq. (9), $$\alpha_L = \frac{\Delta\alpha_L - (a_2/l)(9-3^y)}{6}. \tag{10}$$

Using second equation of Eq. (7) and Eq. (10), the gas parameter is given by $$G=\sqrt{\gamma M}=B[\Delta\alpha_L-(a_2/l)(9-3^y)] \tag{11}$$

Coefficient A and term d caused by device loss can be determined by calibration. To determine A and d, the leakage factor $\Delta\alpha_L$ is first measured at $T_1$ and $P_1$ for a gas having a gas parameter $G_1$ and secondly at $T_2$ and $P_2$ for a gas having a gas parameter $G_2$. Thus, $G_1=A(T_1^{1/2}/P_1)(\Delta\alpha_{L,1}-d)$ and $G_2=A(T_2^{1/2}/P_2)(\Delta\alpha_{L,2}-d)$ giving $$A=(P_2G_2/T_2^{1/2}-P_1G_1/T_1^{1/2})/(\Delta\alpha_{L,2}-\Delta\alpha_{L,1}) \text{ and}$$

$$d=\Delta\alpha_{L,1}-P_1G_1/(AT_1^{1/2}) \tag{12}$$

In the second measurement, all parameters $(T_2, P_2, G_2)$ do not have to be changed from $(T_1, P_1, G_1)$. Different gas species can be measured at the same temperature and the same pressure, that is, calibration-condition $(T_2=T_1, P_2=P_1, G_2 \neq G_1)$ or only the pressure is changed, that is, calibration-condition $(T_2=T_1, P_2 \neq P_1, G_2=G_1)$. In an environment with constant temperature T or pressure P, calibration can be made by $$G=B(\Delta\alpha_L-d), \tag{13}$$

with $$B=A(T^{1/2}/P). \tag{14}$$

Since the leaky attenuation is proportional to the first frequency $F_1$ and the second frequency $F_2$ when z is equal to 1 in Eqs. (5) and (6), it will be cancelled in a viscoelastic factor $\Delta\alpha_V$ defined and given by $$\Delta\alpha_V \equiv [\alpha_2 - (F_2/F_1)\alpha_1]/l \tag{15}$$

$$= [a_1(w)/l](F_2^2 - F_1F_2) + (a_2/l)$$

$$(F_2^y - F_1^{y-1}F_2).$$

In a special case of $F_2=3F_1$, $F_1=1$, $$\Delta\alpha_V=6[a_1(w)/l]+(a_2/l)(3^y-3). \tag{16}$$

First Example

<Measurement of Background Gas>

Figure 6:
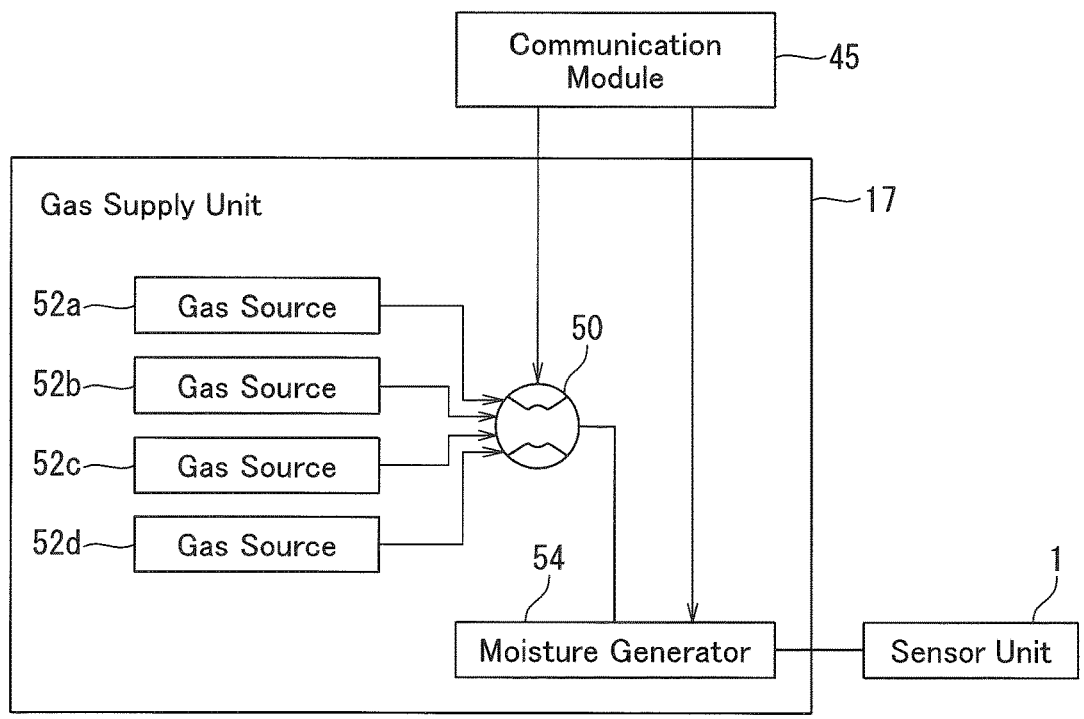
FIG. 6 is a block diagram illustrating an example of the gas supply unit in the system for the gas analysis according to the embodiment of the present invention.

Test measurements for gas analysis of background gases have been executed using a humid gas in which trace moisture as a sensing gas has been mixed in various background gases. The gas supply unit 17 used for the test measurement, as illustrated in FIG. 6, includes a plurality of gas sources 52a, 52b, 52c, 52d, a gas controller 50 and a moisture generator 54. Each of the gas sources 52a, 52b, 52c, 52d includes a gas container of a background gas and a flow controller for controlling a flow rate of the background gas, and supplies the background gas to the sensor unit 1 through the gas-switching valve 50 and the moisture generator 54. Note that, in FIG. 6, the velocity measurement unit 18 is omitted for convenience of explanation. In the test measurement, for example, the gas source 52a supplies a nitrogen ($N_2$) gas, the gas source 52b supplies an argon (Ar) gas, the gas source 52c supplies a methane ($CH_4$) gas, and the gas source 52d supplies air. The gas-switching valve 50 switches to select the background gas from the gas sources 52a, 52b, 52c, 52d by instructions of the communication module 45 of the waveform data processor 44. The moisture generator 54 generates the trace moisture as the sensing gas in the background gas at a predetermined concentration by instructions of the communication module 45 illustrated in FIG. 5. Thus, the humid gas at a predetermined frost point, or a predetermined water concentration can be supplied to the sensor unit 1.

In the test measurement, the fundamental wave and the third-order harmonic wave of the SAW, that is, $f_2=3f_1$, has been used. Each procedure of the test measurements will be described with reference to the flowchart illustrated in FIG. 7. In addition, in the test measurement, the background gas has been assigned as a "target gas" in the humid gas.

In step S100, the gas supply unit 17 supplies the humid gas with the background gas, which is selected from the gas sources 52a to 52d, into the sensor unit 1. In step S101, the signal generator 42a of the signal generator/receiver 42 transmits the burst signal to the SAW sensor 2, so as to excite the collimated beam 21 of the SAW as illustrated in FIGS. 1-3. In step S102, after the collimated beam 21 has propagated a predetermined number of turns around the ball sensor 2, the signal receiver 42b of the signal generator/receiver 42 receives the returned burst signals of the collimated beam 21 through the ball sensor 2. Waveform data of the returned burst signals is transmitted to the waveform data processor 44.

In step S103, the waveform data processor 44 measures a first attenuation $\alpha_1$ of a first burst signal having the first frequency $f_1$ and a second attenuation $\alpha_2$ of a second burst signal having the second frequency $f_2$. In step S104, the waveform data processor 44 calculates the target gas parameter G of the target gas using the leaky attenuation coefficient $\alpha_L$ and the leakage factor $\Delta\alpha_L$, which is derived by the first and second attenuations $\alpha_1$ and $\alpha_2$ using Eqs. (4) and (11). Then, in Step S105, the waveform data processor 44 estimates a gas species of the target gas by comparing the measured gas parameter with the true gas parameters, or the reference gas parameters, which are calculated by the physical-property data of gases. In addition, the waveform data processor 44 measures the viscoelastic factor $\Delta\alpha_V$ of the target gas using Eq. (15) so as to calculate a concentration of the sensing gas.

<Calibration>

Figure 9:
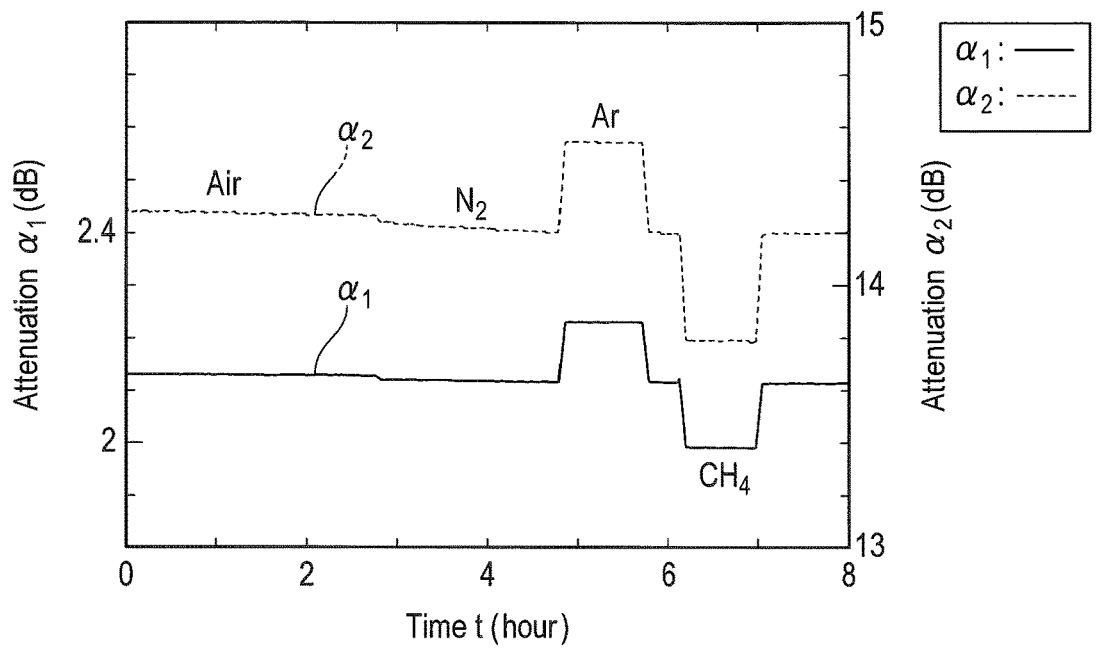
FIG. 9 is a diagram illustrating examples of attenuations of the SAWs at frequencies $f_1$ and $f_2$ by changing background gases according to a first example of the embodiment of the present invention.
Figure 10:
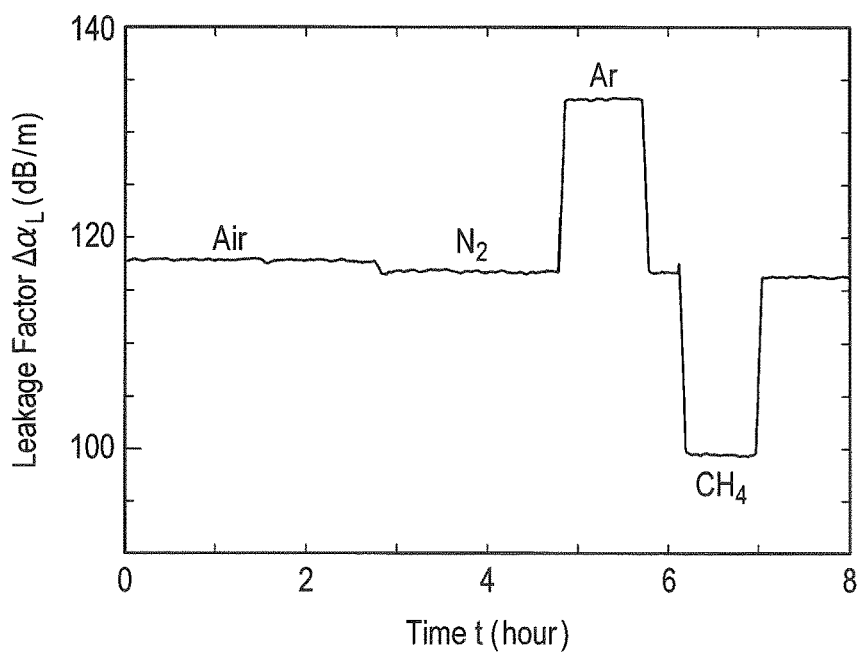
FIG. 10 is a diagram illustrating examples of leakage factors of the SAWs by changing the background gases according to the first example of the embodiment of the present invention.
Figures 11, 12:
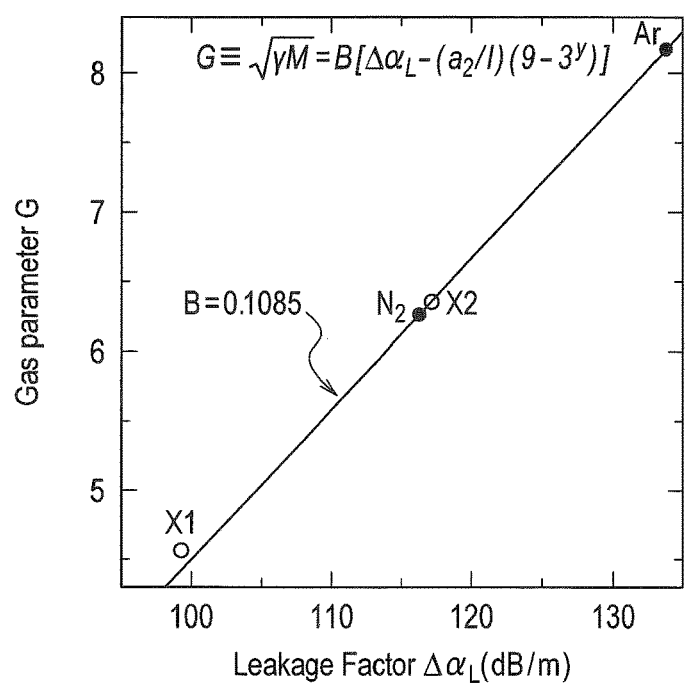
FIG. 11 is a table illustrating examples of the measured gas parameters for the background gases according to the first example of the embodiment of the present invention.
FIG. 12 is a diagram illustrating an example of a relationship between the leakage factor and a gas parameter according to the first example of the embodiment of the present invention.

An example of calibration for the coefficient B and the term d in Eqs. (13) and (14) will be described below. In the calibration procedure, a humid gas having frost point of −60° C. or water concentration of 10.7 ppmv has been used with background gases of Air, $N_2$, Ar and $CH_4$ which have been supplied from the gas source 52a to 52d of the gas supply unit 17 illustrated in FIG. 6. In the humid gas, the background gas has been changed in order of Air, $N_2$, Ar and $CH_4$, and the first and second attenuations $\alpha_1$ and $\alpha_2$ have been measured, as illustrated in FIG. 9. Then, the leakage factor $\Delta\alpha_L$ has been measured using the first and second attenuations $\alpha_1$ and $\alpha_2$, as plotted in FIG. 10. In the measurement, the propagation length l of the SAW has been set to be l=41.47 mm. In the case of the calibration using $N_2$ and Ar, the relation between gas parameters G and the leakage factors $\Delta\alpha_L$, which have been calculated using the known values of gas parameters G for $N_2$ and Ar, has been plotted as closed circles in FIG. 12. Extrapolating a straight line connecting two closed circles extending to G=0 with M=0, the coefficient B and the term d caused by device loss in Eqs. (13) and (14) have been calibrated as B=0.1085 and d=58.53 dB/m.

<Estimation of Background Gas-1>

Assuming that the first background gas and the fourth background gas in FIG. 9 are unknown, let the first and the fourth background gases, which are air and $CH_4$, be target gases X2 and X1, respectively. Then, the target gases X2 and X1 have been estimated by using the gas analyzer pertaining to the embodiment of the present invention as illustrated in FIG. 1.

Using Eq. (11) with the calibrated parameter B, measured gas parameters G*, or target gas parameters G* of the target gases X1 and X2 have been measured, as 4.43 and 6.36 as listed in a table of FIG. 11. Comparing with the gas parameters G listed in the table illustrated in FIG. 8, which will be denoted by the "true gas parameters" below, it has been understood that the values of the measured gas parameters G* of the target gases X1 and X2 have been most close to the true gas parameter 4.56 of $CH_4$ and the true gas parameter 6.35 of Air. Thus, the target gases X1 and X2 can be estimated to be $CH_4$ and Air, respectively. The open circles, which indicates the measured gas parameters G* of the target gases X1, X2, are close to the calibration straight line illustrated in FIG. 12 and the measurement error from the true gas parameters G has been evaluated as −2.89% and 0.228%, respectively, as listed in the table illustrated in FIG. 11.

<Estimation of Background Gas-2>

Figure 13:
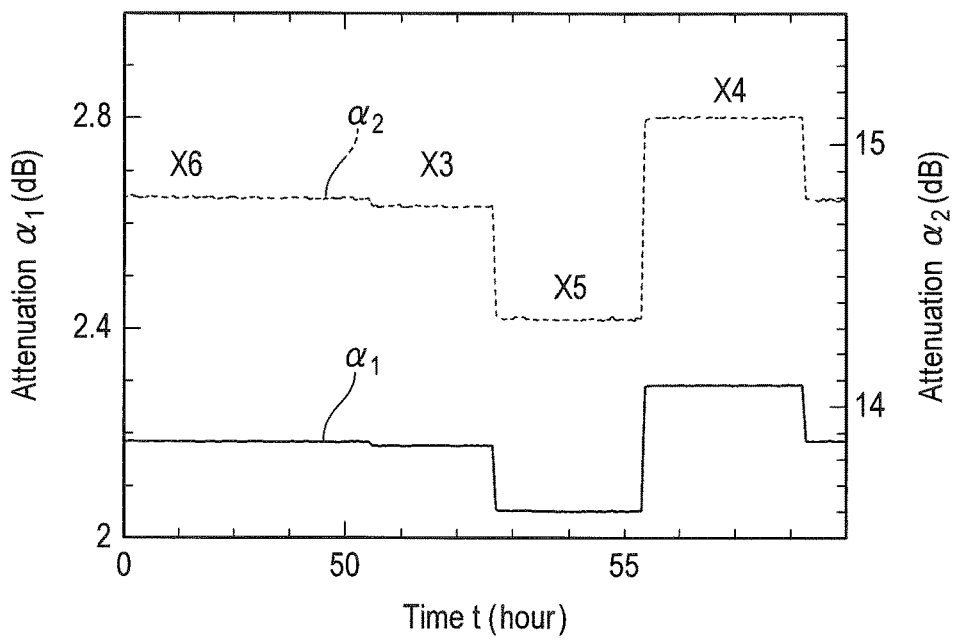
FIG. 13 is a diagram illustrating other examples of attenuations of the SAWs at frequencies $f_1$ and $f_2$ by changing background gases according to the first example of the embodiment of the present invention.
Figure 14:
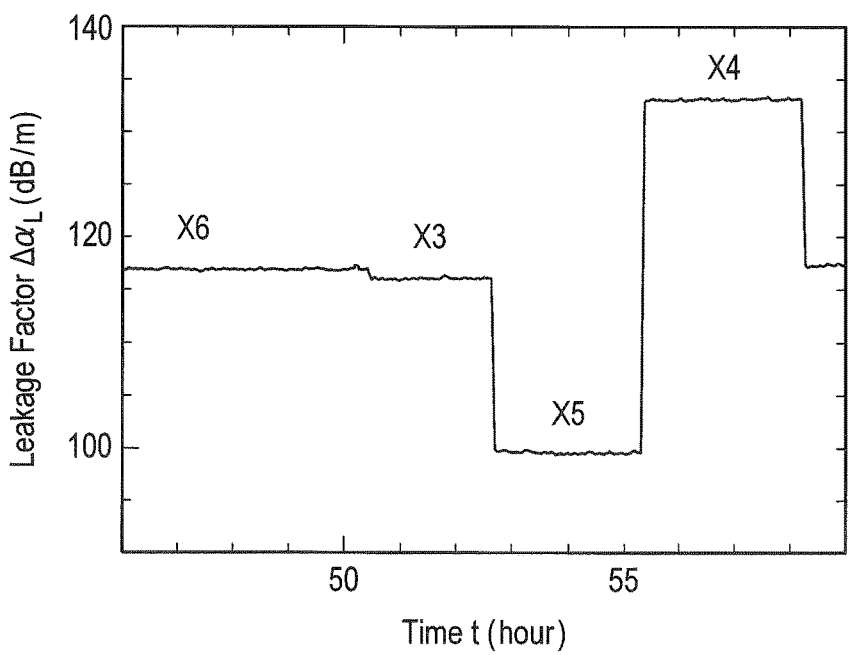
FIG. 14 is a diagram illustrating other examples of leakage factors of the SAWs by changing the background gases according to the first example of the embodiment of the present invention.
Figures 15, 16:
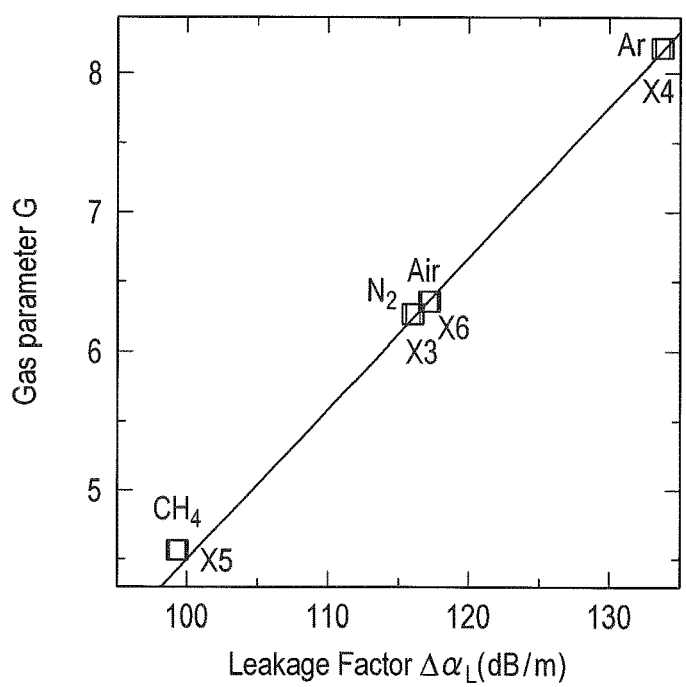
FIG. 15 is a table illustrating other examples of measured gas parameters for the background gases according to the first example of the embodiment of the present invention.
FIG. 16 is a diagram illustrating another example of the relationship between the leakage factor and the gas parameter according to the first example of the embodiment of the present invention.

In a humid gas having another humidity of frost point of −50° C. and water concentration of 38.8 ppmv, the background gases X3, X4, X5, X6 have been used as target gases. The background gas has been changed in order of X6, X3, X5 and X4, as illustrated in FIG. 13, and the leakage factor $\Delta\alpha_L$ has been measured as illustrated in FIG. 14. Since the measured gas parameters G* of the background gases X3, X4, X5, X6, listed in a table of FIG. 15, are very close to the true gas parameters G of 6.26, 8.17, 4.56 and 6.35, which correspond to $N_2$, Ar, $CH_4$ and Air, the target gases can be estimated to be X3=$N_2$, X4=Ar, X5=$CH_4$ and X6=Air, respectively. The measured gas parameters G* has been very close to an extrapolated straight line in FIG. 16, and the measurement error has been less than 2.7% as illustrated in the table illustrated in FIG. 15.

Figure 17:
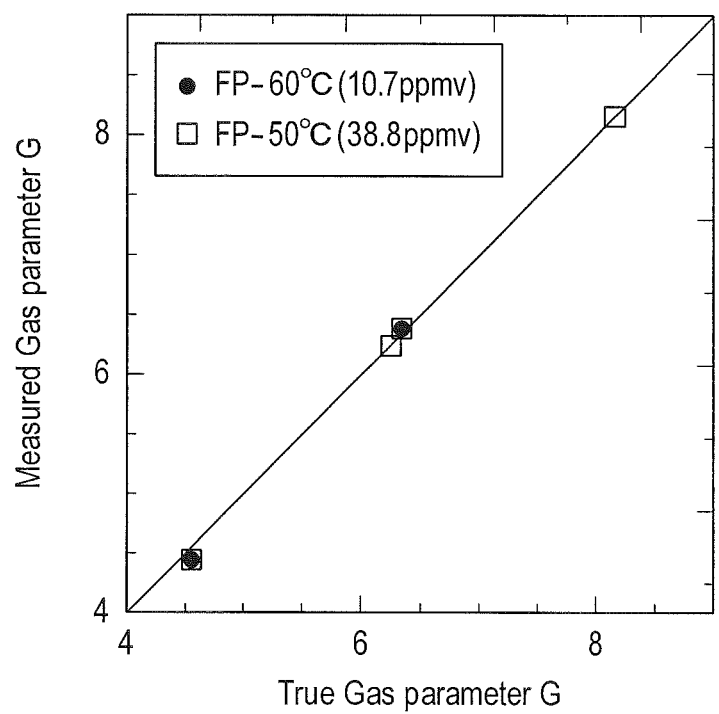
FIG. 17 is a diagram illustrating the summarized gas parameters measured by the gas analyzer according to the embodiment of the present invention.

The measured gas parameters G* and the true gas parameters G are summarized in a graph illustrated in FIG. 17. The agreement between the measured gas parameters G* and the true gas parameters G is significant. The result of the graph of FIG. 17, which indicates that the measurement of the background gas is not disturbed by changing the humidity as the sensing gas, provides the accuracy of the gas analyzer according to the embodiment of the present invention.

<Measurement of Sensing Gas>

Figure 18:
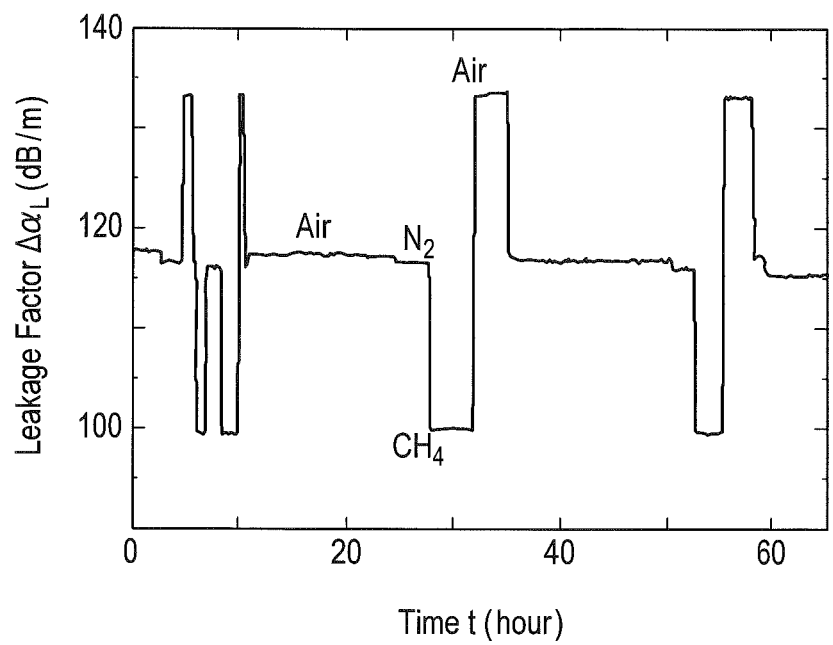
FIG. 18 is a diagram illustrating examples of leakage factors of the SAW by changing the background gases according to a first modification of the embodiment of the present invention.
Figure 19:
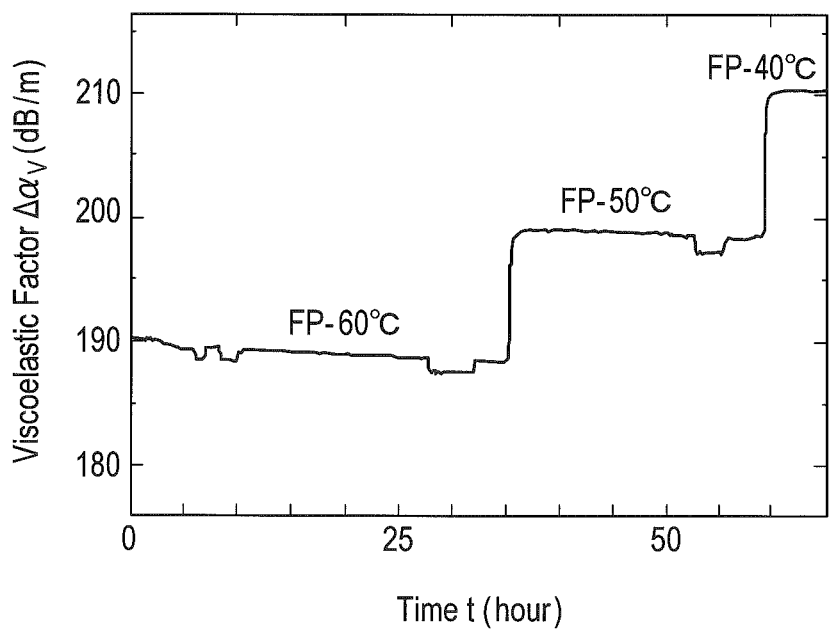
FIG. 19 is a diagram illustrating examples of viscoelastic factors of the SAW by changing the background gases according to the first modification of the embodiment of the present invention.

In the gas analyzer according to the embodiment of the present invention, it is also possible to measure a concentration of the sensing gas in the background gas with high precision using the viscoelastic factor $\Delta\alpha_V$, even when composition of the background gas is changed. To verify that the viscoelastic factor $\Delta\alpha_V$ does not depend on the background composition but only on the moisture content, the leakage factor $\Delta\alpha_L$ evaluated using Eq. (4) and the viscoelastic factor $\Delta\alpha_V$ evaluated using Eq. (15) have been compared in a wide time range of about 65 hours using humid gases having the frost points of −60° C., −50° C. and −40° C., which correspond to 10.7 ppmv, 38.8 ppmv and −127 ppmv, as illustrated in FIGS. 18 and 19. Then, it is confirmed that the leakage factor $\Delta\alpha_L$ is independent of the moisture content, as illustrated in FIG. 18. In contrast, as illustrated in FIG. 19, the viscoelastic factor $\Delta\alpha_V$ is almost independent on the change in the background composition and represents only the change in moisture content. Thus, the viscoelastic factor $\Delta\alpha_V$ is useful for the moisture measurement under different background gases without time-consuming recalibration procedure for each background gas.

Second Example

In the following explanation of the second example, each of M(bar), G(bar), γ(bar), $C_p$(bar) and $C_V$(bar), etc. represents a symbol labeled with an horizontal over line, or an over bar on the top of the characters of M, γ, $C_p$ and $C_v$, etc.

<Application to Mixed Gas>

In a mix gas having a plurality of component gases, an average gas parameter G(bar) is given by $$G(bar) = \{\gamma(bar)M(bar)\}^{1/2} = [C_P(bar)/C_V(bar)]^{1/2}M(bar) \quad (17)$$

where M(bar) is average molecular weight and γ(bar) is average ratio of average specific heat $C_p$(bar) at constant pressure to average specific heat $C_V$(bar) at constant volume. M(bar), $C_p$(bar) and $C_v$(bar) are given by $$M(bar) = \sum_{i=1}^{N} x_i M_i, C_P(bar) = \sum_{i=1}^{N} x_i C_{Pi}, C_V(bar)$$
$$= \sum_{i=1}^{N} x_i C_{Vi}, \sum_{i=1}^{N} x_i = 1 \quad (18)$$

where $M_i$, $C_{Pi}$, $C_{Vi}$, $x_i$ and N are molecular weight, specific heat at constant pressure, specific heat at constant volume, molar fraction of each component gas i and number digit of component gases, respectively.

In the case of two background gases of XA and XB, G(bar) is derived as $$G(bar) = \{[(C_{PA} - C_{PB})x + C_{PB}][(M_A - M_B)x + M_B]/[(C_{VA} - C_{VB})x + C_{VB}]\}^{1/2} \quad (19)$$

where x is the concentration by mole percentage, or mol %, of gas XA, $M_A$, $C_{PA}$ and $C_{VA}$ are molecular weight, specific heat at a constant pressure and specific heat at constant volume of the gas XA, and $M_B$, $C_{PB}$, $C_{VB}$ are molecular weight, specific heat at a constant pressure and specific heat at constant volume of the gas XB, respectively.

To verify Eq. (19), helium (He) as the gas XA has been mixed with $N_2$ as gas XB, where molecular weight, specific heat at a constant pressure, specific heat at constant volume, ratio of specific heats and gas parameter of He and $N_2$ are listed in FIG. 20. The measurement sequence was performed in which He concentration has been increased from 0% to 100% with 10% steps and decreased from 100% to 0% with 10% steps. The measurement time of each step has been 20 min.

Figures 20, 21:
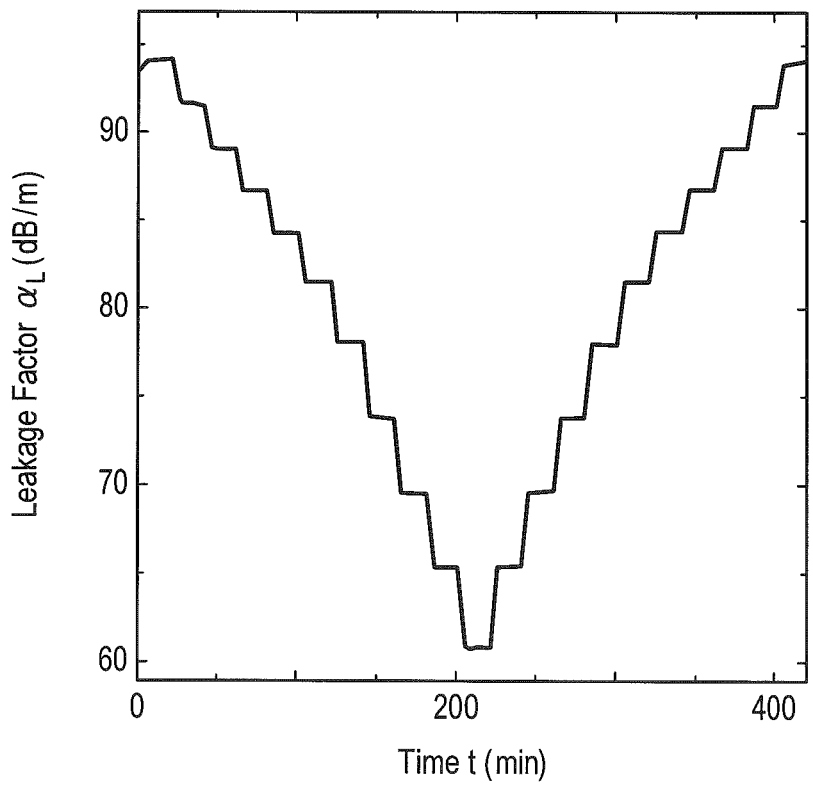
FIG. 20 is a table illustrating properties of He and $N_2$ according to a second modification of the embodiment of the present invention.
FIG. 21 is a diagram illustrating an example of a leakage factor by changing the He concentration in mix gas of He and $N_2$ according to the second modification of the embodiment of the present invention.
Figure 22:
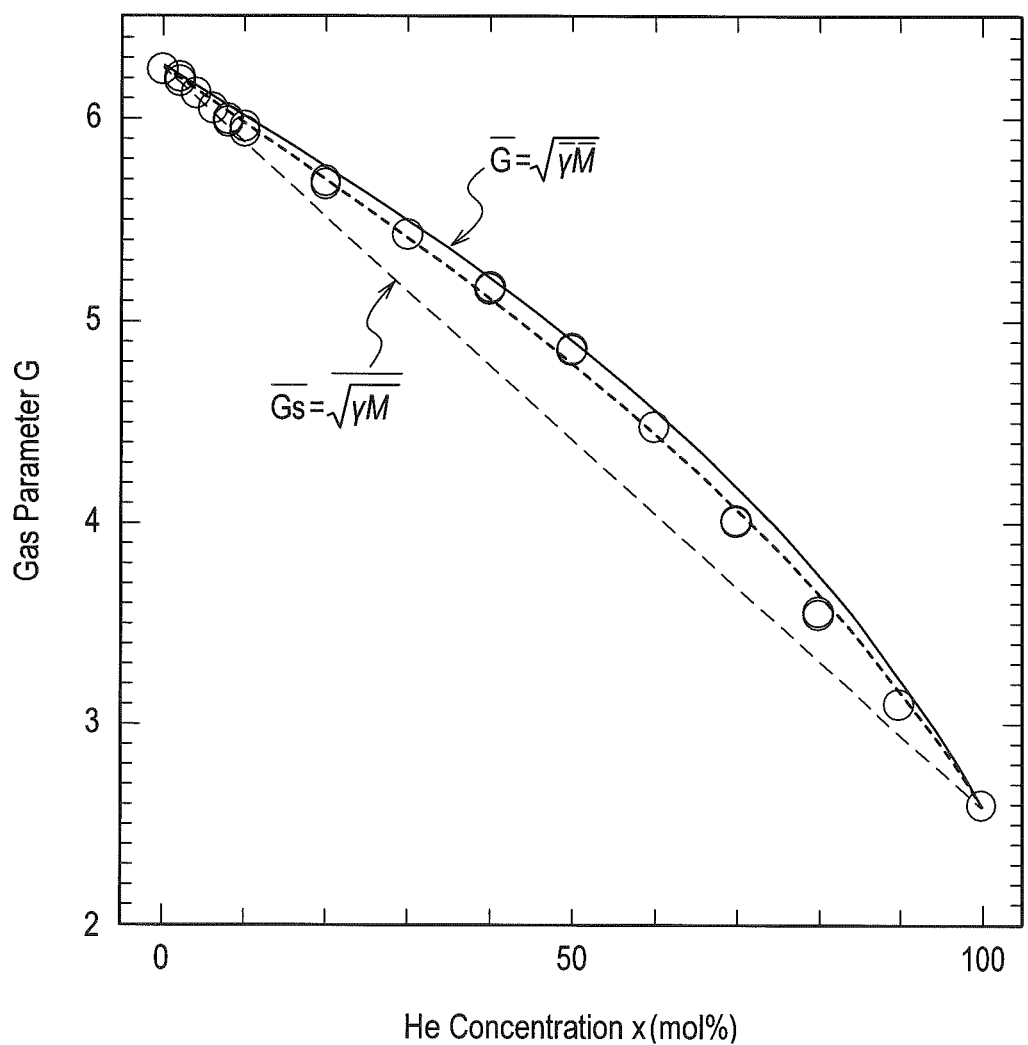
FIG. 22 is a diagram illustrating an example of a gas parameter against He concentration according to the second modification of the embodiment of the present invention.

The measured leakage factor $\alpha_L$ in the measurement sequence is plotted against time in FIG. 21. Then, the average gas parameter G(bar) has been calculated over the last ten minutes of each step, and plotted by open circles against the He concentration in FIG. 22. The measured values of the average gas parameter G(bar) agree well with a calculated curve, illustrated by solid curve in FIG. 22, using Eq. (19) with parameters listed in FIG. 20. Note that the calculated curve of the average gas parameter G(bar) in FIG. 22 does not agree with a simple average of the average gas parameter $$G_S(bar) = \{\gamma M\}^{1/2}(bar) \quad (20)$$

of He and $N_2$, illustrated by dashed line in FIG. 22.

The concentration of He can be measured by the average gas parameter G(bar) with using a calibration curve. The calibration curve may be calculated by replacing $C_{PB}$ with $\beta C_{PB}$ and $C_{VB}$ with $\beta C_{VB}$ in Eq. (19) where the β is an adjustable parameter. The replacement does not change the average gas parameter G(bar) at the molar fraction x=0 or at the molar fraction x=1 but changes the average gas parameter G(bar) in the intermediate range of the molar fraction x from 0.1 to 0.9, that is, 10 mol % to 90 mol %. Though the adjustable parameter β has no physical meaning, the adjustable parameter β helps to improve the agreement between the experimental data and the calibration curve when the adjustable parameter β is set to 3.0, as illustrated by dotted curve in FIG. 22, which is slightly deformed and shifted from the solid curve.

Figure 23:
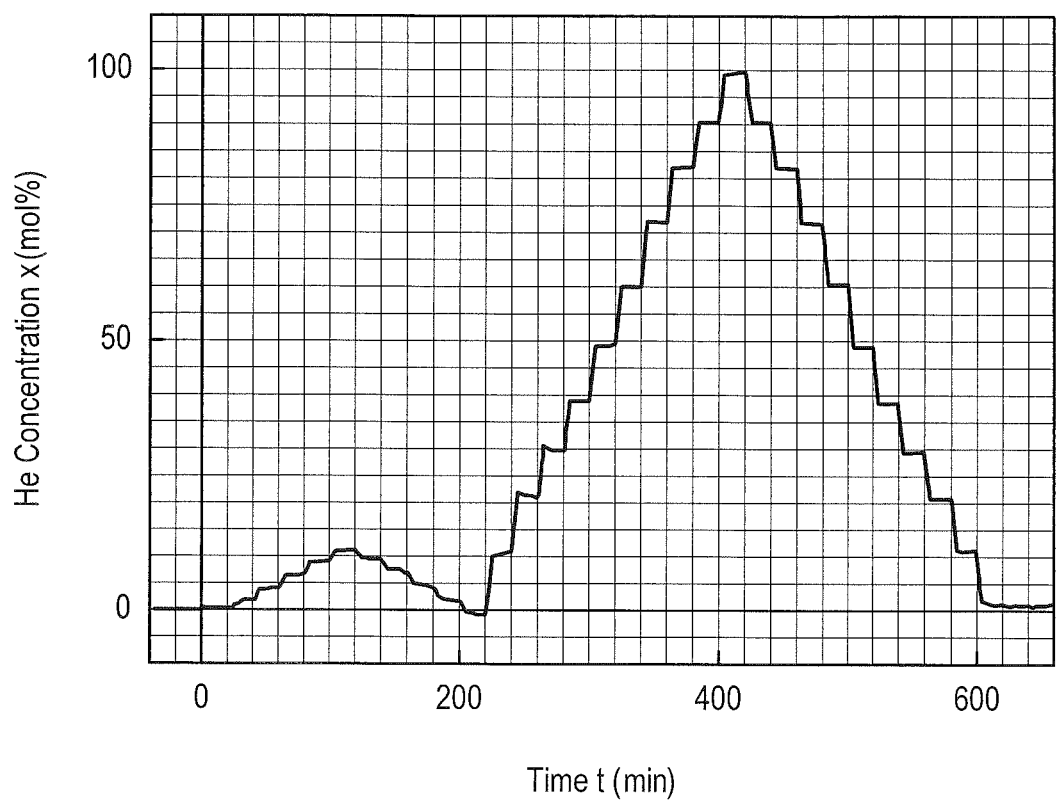
FIG. 23 is a diagram illustrating an example of measured He concentration by changing the set He concentration in mix gas of He and $N_2$ according to the second modification of the embodiment of the present invention.
Figure 24:
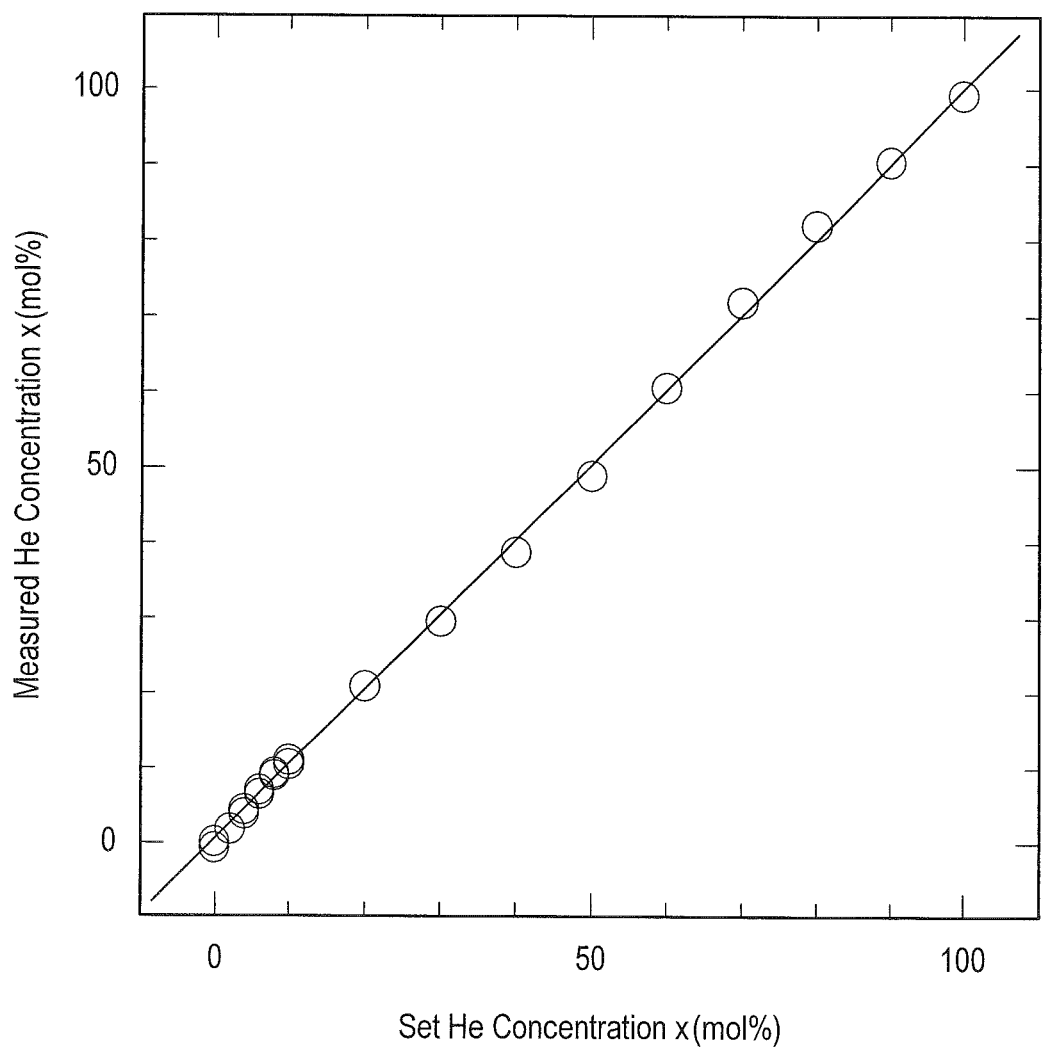
FIG. 24 is a diagram illustrating an example of comparison between the measured concentration and the set concentration of He according to the second modification of the embodiment of the present invention.

Using the calibration curve, He concentration has been measured as illustrated in FIG. 23, where set concentration has been increased in order from 0 mol % to 10 mol % by 2 mol % steps, decreased from 10 mol % to 0 mol % by 2 mol % steps, increased from 0 mol % to 100 mol % by 10 mol % steps and decreased from 100 mol % to 0 mol % by 10 mol % steps. The measured concentration has been compared with the set concentration and it has been confirmed that good agreement between the set concentration and measured concentration has been obtained as illustrated in FIG. 24. The standard deviation of the measured concentration from the set concentration has been about 0.96% in the measurement of He 0 mol % to 100 mol %. Thus, in the gas analyzer according to the embodiment of the present invention, it is possible to measure the concentration of the component gas in the mix gas with high precision.

<Application to Glove Box>

Further, it is also possible to apply the gas analyzer according to the embodiment of the present invention for checking whether an interior of a glove box has been replaced with a purge-gas. For example, the glove box used for Li-ion batteries or for 3D printers of metal objects, it is required to replace air and moisture in the glove box with the purge-gas. For the purge-gas, an inert gas, such as argon, helium, $N_2$ and the like, or a mixture of inert gases may be preferably used to avoid unwanted chemical reactions with oxygen ($O_2$) in the air and the moisture. While purging the air and the moisture by introducing the purge-gas into the glove box, the purge-gas and the air may be implemented by the mix gas and concentration of the purge-gas may increase with time. Thus, it is possible to measure the concentration of the purge-gas as a component gas, which is mixed with the air in the glove box, using the gas parameter G(bar) of Eq. (19). Also, it is expected to be precise enough for the measurement of the spatial distribution of the purge-gas in the glove box. In addition, concentration of the moisture in the glove box may be also measured as the sensing gas using the viscoelastic factor $\Delta\alpha_V$ of Eq. (15).

<Measurement of Average Molecular Weight and Average Specific Heat Ratio>

With Mayer's relationship, $C_{pi} = C_{Vi} + R$, Eq. (19) is replaced by $$M(bar) = \sum_{i=1}^{N} x_i M_i, C_P(bar) = \sum_{i=1}^{N} x_i (C_{Vi} + R), C_V(bar)$$
$$= \sum_{i=1}^{N} x_i C_{Vi}, \sum_{i=1}^{N} x_i = 1. \quad (21)$$

The average sound velocity V(bar) is usually measured in gas analysis as, $$V(bar) = [\gamma(bar)RT/M(bar)]^{1/2} = \{[1 + R/(C_V(bar))]RT/M(bar)\}^{1/2} \quad (22)$$

In Eq. (22), independent quantity of molecular weight nor ratio of specific heat is not available. However, when the gas analyzer gives a gas parameter G(bar) in Eq. (17), the average molecular weight M(bar) and the average specific heat ratio γ(bar) are independently solved from Eq. (17) and Eq. (22) as $$M(bar) = \sum_{i=1}^{N} x_i M_i = G(bar)(RT)^{1/2}/V(bar) \text{ and}$$

$$\gamma(bar) = \sum_{i=1}^{N} x_i (C_{Vi} + R)/\sum_{i=1}^{N} x_i C_{Vi} = G(bar)V(bar)/(RT)^{1/2}. \quad (23)$$

The average molecular weight M(bar) and the average specific heat ratio γ(bar) are useful for calculation of many physical/chemical property of the mix gas.

To obtain molar fraction $x_i$ (i=1, N) of each component gas, N independent equations are required.

In a special case of N=3, measurements for the average gas parameter G(bar) and the average sound velocity V(bar) results in, $$x_1 M_1 + x_2 M_2 + x_3 M_3 = G(bar)(RT)^{1/2}/V(bar) \quad (24)$$

$$[x_1(C_{V1}+R)+x_2(C_{V2}+R)+x_3(C_{V3}+R)]/(x_1C_{V1}+x_2C_{V2}+x_3C_{V3})=G(\text{bar})V(\text{bar})/(RT)^{1/2}, \text{ and} \quad (25)$$

$$x_1+x_2+x_3=1. \quad (26)$$

Linear simultaneous Eqs. (24), (25) and (26) can be solved for molar fraction ($x_1$, $x_2$, $x_3$).

(Case A)

When hydrogen is injected to a mix gas of natural gases, for example, methane and ethane, and $x_1$=[$H_2$], $x_2$=[$CH_4$], $x_3$=[$C_2H_6$], mole fraction ($x_1$, $x_2$, $x_3$) is solved by Eqs. (24) to (26).

(Case B)

When hydrogen is injected to methane, and $x_1$=[$H_2$], $x_2$=[$CH_4$], $$G(\text{bar})=\{[x_1(C_{V1}+R)+x_2(C_{V2}+R)](x_1M_1+x_2M_2)/(x_1C_{V1}+x_2C_{V2})\}^{1/2} \quad (27)$$

$$x_1+x_2=1. \quad (28)$$

Then, molar fraction ($x_1$, $x_2$) is solved by Eqs. (27) and (28).

(Measurement of Density and Compressibility)

As illustrated in FIGS. 1 and 5, the gas analyzer according to the embodiment can measure a sound velocity of the gas by the velocity measurement unit 18 using an ultrasonic wave having a frequency in a range of 10 kHz to 100 kHz. The average sound velocity is expressed by average density $\rho(\text{bar})$ and average compressibility $K_G$ (bar), as $$V(\text{bar})=\{1/[\rho(\text{bar})K_G(\text{bar})]\}^{1/2} \quad (29)$$

In such case, it is useful to express the average leaky attenuation coefficient $\alpha_L(\text{bar})$ as $$\alpha_L(\text{bar})=f[\rho(\text{bar})/K_G(\text{bar})]^{1/2}/[\rho_S V_S^2] \quad (30)$$

similarly to Eq. (1). Then, from Eqs. (29) and (30), the average compressibility and the average density are solved as $$K_G(\text{bar})=\{f/[\rho_S V_S^2]\}\{1/[V(\text{bar})\alpha(\text{bar})]\} \quad (31)$$

$$\rho(\text{bar})=\{[\rho_S V_S^2]/f\}\{\alpha_L(\text{bar})/V(\text{bar})\}. \quad (32)$$

The average leaky attenuation coefficient $\alpha_L(\text{bar})$ is calculated by, $$\alpha_L(\text{bar})=\{\Delta\alpha_L-(a_2/l)(9-3^y)\}/6. \quad (33)$$

similarly to Eq. (10).

The average molecular weight and the average specific heat ratio can not be separated by merely measuring the average gas parameter. However, by adding measurement of the average sound velocity of the mix gas, it is possible to independently measure the average molecular weight and the average specific heat ratio. Thus, there is an advantage that other thermodynamic quantities can be calculated by independently measuring the average molecular weight and the average specific heat ratio.

Other Embodiments

While the present invention has been described above by reference to the embodiment, it should be understood that the present invention is not intended to be limited to the descriptions of the specification and the drawings implementing part of this disclosure. Various alternative embodiments, examples, and technical applications will be apparent to those skilled in the art according to this disclosure. It should be noted that the present invention includes various embodiments which are not disclosed herein. Therefore, the scope of the present invention is defined only by the present invention specifying matters according to the claims reasonably derived from the description heretofore.

REFERENCE SIGNS LIST 1 sensor unit
2 SAW sensor (ball SAW sensor)
2a planar SAW sensor
10 temperature control unit
11 holder
12 Peltier element
13 thermistor
14 adapter
16 temperature controller
17 gas supply unit
18 velocity measurement unit
20 piezoelectric ball
20a piezoelectric substrate
21 collimated beam
22 sensor electrode
22a input electrode
22b output electrode
23, 23a sensitive film
31 sensor cell
32 electrode-holder base
33 sensor-cell cap
34 electrode holder
35 external electrode
36 tubing
40 signal processing unit
42 signal generator/receiver
42a signal generator
42b signal receiver
44 waveform data processor
45 communication module
46 calculation module
47 comparison module
48 memory unit
50 gas-switching valve
52a, 52b, 52c, 52d gas source
54 moisture generator

The invention claimed is:

1. A system for gas analysis, comprising:
a sensor having:
a piezoelectric substrate,
a sensor electrode configured to generate a collimated beam of a surface acoustic wave of first and second frequencies, which propagates on the piezoelectric substrate, and
a sensitive film configured to adsorb a sensing gas contained in a background gas, the sensitive film is deposited in a position where the collimated beam passes through; and
a signal processing unit having:
a signal generator configured to transmit an exciting burst signal to the sensor electrode so as to excite the collimated beam,
a signal receiver configured to receive first and second returned burst signals of the collimated beam through the sensor electrode after the collimated beam has propagated on the piezoelectric substrate, the first returned burst signal having the first frequency and the second returned burst signal having the second frequency, and
a data processor configured to calculate a target gas parameter both by a target leakage factor of the background gas and by a relation between reference gas parameters and reference leakage factors of reference gases, the target leakage factor is calculated by a first attenuation of the first returned burst signal and a second attenuation of the second returned burst signal using waveform data of the first and second returned burst signals, wherein the target leakage factor and the target gas parameter are given by, $$\Delta\alpha_L \equiv [(f_2/f_1)^u \alpha_1 - \alpha_2]/l, \text{ and}$$

$$G = A(T^{1/2}/P)(\Delta\alpha_L - d)$$

where, $\Delta\alpha_L$ is the target leakage factor and G is the target gas parameter, respectively, $f_1$ and $f_2$ are the first and second frequencies, respectively, $\alpha_1$ and $\alpha_2$ are the first and second attenuations, respectively, u is a real number satisfying $1.8 \leq u \leq 2.3$, and l is a propagation length of the surface acoustic wave, T and P are temperature and pressure of the background gas, respectively, and A and d are a coefficient and a term caused by a loss of the sensor, respectively.

2. The system of claim 1, wherein each of the reference gas parameters is provided as a square root of a product of molecular weight of each of the reference gases and a ratio of specific heat at constant pressure to specific heat at constant volume of said each of the reference gases, and each of the reference leakage factors is provided by a first reference attenuation of a first reference burst signal and a second reference attenuation of a second reference burst signal using waveform data of a reference burst signals.

3. The system of claim 1, wherein the data processor compares the target gas parameter with the reference gas parameters so as to estimate a gas species of the background gas.

4. The system of any one of claim 1, wherein the data processor measures a viscoelastic factor of the background gas so as to calculate a concentration of the sensing gas, the viscoelastic factor is provided by the first attenuation and the second attenuation.

5. The system of claim 4, wherein, the viscoelastic factor is given by, $$\Delta\alpha_V \equiv [\alpha_2 - (f_2/f_1)^z \alpha_1]/l,$$

where, $\Delta\alpha_V$ is the viscoelastic factor, $f_1$ and $f_2$ are the first and second frequencies, respectively, $\alpha_1$ and $\alpha_2$ are the first and second attenuations, respectively, z is a real number satisfying $0.8 \leq z \leq 1.3$, and l is a propagation length of the surface acoustic wave.

6. The system of claim 1, wherein, the background gas includes a plurality of component gases, and each of the reference gas parameters is defined as a square root of a product of an average molecular weight and a ratio of an average specific heat at constant pressure to an average specific heat at constant volume of each of the component gases.

7. The system of claim 6, wherein the background gas is a mixture of two component gases and the data processor calculates a concentration of anyone of the component gases by the reference gas parameters.

8. The system of claim 7, wherein the background gas is a mixture of a natural gas and hydrogen injected in the natural gas.

9. The system of claim 6, further comprising a velocity measurement unit configured to measure a sound velocity of the background gas, wherein the data processor calculates an average leaky attenuation coefficient by the target leakage factor and an average sound velocity of the background gas measured using the velocity measurement unit, and the data processor calculates an average compressibility of the background gas and an average density of the background gas by the average leaky attenuation coefficient and the average sound velocity.

10. The system of claim 9, wherein the data processor further calculates an average molecular weight and an average ratio of specific heat by the average gas parameter and the average sound velocity.

11. A method for gas analysis using a surface acoustic wave sensor having a sensor electrode generating a surface acoustic wave and a sensitive film adsorbing a sensing gas, on a piezoelectric substrate, comprising:

flowing a background gas containing the sensing gas into a sensor cell having the surface acoustic wave sensor in place;

transmitting an exciting burst signal to the sensor electrode so as to excite a collimated beam of the surface acoustic wave of first and second frequencies, which propagates on the piezoelectric substrate while passing through the sensitive film deposited in a position where the collimated beam passes through;

receiving first and second returned burst signals of the collimated beam through the sensor electrode after the collimated beam has propagated on the piezoelectric substrate, the first returned burst signal having the first frequency and the second returned burst signal having the second frequency; and calculating a target gas parameter by a target leakage factor of the background gas and a relation between reference gas parameters and reference leakage factors of reference gases, the leakage factor is provided by a first attenuation of the first returned burst signal and a second attenuation of the second returned burst signal using waveform data of the first and second returned burst signals, wherein the target leakage factor and the target gas parameter are given by, $$\Delta\alpha_L \equiv [(f_2/f_1)^u \alpha_1 - \alpha_2]/l, \text{ and}$$

$$G = A(T^{1/2}/P)(\Delta\alpha_L - d)$$

where, $\Delta\alpha_L$ is the target leakage factor and G is the target gas parameter, respectively, $f_1$ and $f_2$ are the first and second frequencies, respectively, $\alpha_1$ and $\alpha_2$ are the first and second attenuations, respectively, u is a real number satisfying $1.8 \leq u \leq 2.3$, and l is a propagation length of the surface acoustic wave, T and P are temperature and pressure of the background gas, respectively, and A and d are a coefficient and a term caused by a loss of the sensor, respectively.

12. The method of claim 11, wherein each of the reference gas parameters is provided as a square root of a product of molecular weight of each of the reference gases and a ratio of specific heat at constant pressure to specific heat at constant volume of said each of the reference gases, and each of the reference leakage factors is provided by a first reference attenuation of a first reference burst signal and a second reference attenuation of a second reference burst signal using waveform data of a reference burst signals.

13. The method of claim 11, further comprising comparing the target gas parameter with the reference gas parameters so as to estimate a gas species of the background gas.

14. The method of any one of claim 12, further comprising measuring a viscoelastic factor of the background gas so as to calculate a concentration of the sensing gas, the viscoelastic factor is provided by the first attenuation and the second attenuation.

15. The method of claim 11, wherein
the background gas includes a plurality of component gases, and
each of the reference gas parameters is defined as a square root of a product of an average molecular weight and a ratio of an average specific heat at constant pressure to an average specific heat at constant volume of each of the component gases.

16. The method of claim 15, wherein the background gas is a mixture of two component gases and further comprising:
calculating a concentration of anyone of the component gases by the reference gas parameters.

17. The method of claim 11, further comprising:
measuring an average sound velocity of the background gas using a velocity measurement unit; and
calculating an average compressibility of the background gas and an average density of the background gas by the average leaky attenuation coefficient and the average sound velocity.

18. The method of claim 17, further comprising calculating an average molecular weight and an average ratio of specific heat by the average gas parameter and the average sound velocity.

19. A computer-readable recording medium having recorded thereon a computer program for gas analysis using a surface-acoustic-wave sensor having a sensor electrode generating a surface-acoustic-wave and a sensitive film adsorbing a sensing gas, on a piezoelectric substrate, the computer program comprising:

instructions to flow a background gas containing the sensing gas into a sensor cell having the surface-acoustic-wave sensor in place;

instructions to transmit an exciting burst signal to the sensor electrode so as to excite a collimated beam of the surface-acoustic-wave of first and second frequencies, which propagates on the piezoelectric substrate while passing through the sensitive film deposited in a position where the collimated beam passes through;

instructions to receive first and second returned burst signals of the collimated beam through the sensor electrode after the collimated beam has propagated on the piezoelectric substrate, the first returned burst signal having the first frequency and the second returned burst signal having the second frequency; and instructions to calculate a target gas parameter by a target leakage factor of the background gas and by a relation between reference gas parameters and reference leakage factors of reference gases, the target leakage factor is provided by a first attenuation of the first returned burst signal and a second attenuation of the second returned burst signal using waveform data of the first and second returned burst signals;

wherein the target leakage factor and the target gas parameter are given by, $$\Delta\alpha_L = [(f_2/f_1)^u \alpha_1 - \alpha_2]/l, \text{ and}$$

$$G = A(T^{1/2}/P)(\Delta\alpha_L - d)$$

where, $\Delta\alpha_L$ is the target leakage factor and G is the target gas parameter, respectively, $f_1$ and $f_2$ are the first and second frequencies, respectively, $\alpha_1$ and $\alpha_2$ are the first and second attenuations, respectively, u is a real number satisfying $1.8 \leq u \leq 2.3$, and l is a propagation length of the surface acoustic wave, T and P are temperature and pressure of the background gas, respectively, and A and d are a coefficient and a term caused by a loss of the sensor, respectively.

* * * * *